(12) United States Patent
Ramanujam et al.

(10) Patent No.: US 9,820,655 B2
(45) Date of Patent: Nov. 21, 2017

(54) SYSTEMS AND METHODS FOR SPECTRAL ANALYSIS OF A TISSUE MASS USING AN INSTRUMENT, AN OPTICAL PROBE, AND A MONTE CARLO OR A DIFFUSION ALGORITHM

(75) Inventors: Nirmala Ramanujam, Chapel Hill, NC (US); Bing Yu, Cary, NC (US); Jonathon Quincy Brown, Morrisville, NC (US)

(73) Assignee: DUKE UNIVERSITY, Durham, NC (US)

( * ) Notice: Subject to any disclaimer, the term of this patent is extended or adjusted under 35 U.S.C. 154(b) by 923 days.

(21) Appl. No.: 12/680,305

(22) PCT Filed: Sep. 29, 2008

(86) PCT No.: PCT/US2008/078186
§ 371 (c)(1),
(2), (4) Date: Dec. 30, 2010

(87) PCT Pub. No.: WO2009/043045
PCT Pub. Date: Apr. 2, 2009

(65) Prior Publication Data
US 2011/0112435 A1    May 12, 2011

Related U.S. Application Data

(60) Provisional application No. 60/995,826, filed on Sep. 28, 2007, provisional application No. 61/047,270, (Continued)

(51) Int. Cl.
*A61B 5/00*    (2006.01)

(52) U.S. Cl.
CPC .......... *A61B 5/0091* (2013.01); *A61B 5/0071* (2013.01); *A61B 5/0075* (2013.01);
(Continued)

(58) Field of Classification Search
CPC ..... A61B 10/02; A61B 5/0059; A61B 5/0071; A61B 5/0086; A61B 5/0075; A61B 5/0084; A61B 5/0091; A61B 5/413; A61B 5/4312
(Continued)

(56) References Cited

U.S. PATENT DOCUMENTS

| | | |
|---|---|---|
| 4,034,884 A | 7/1977 | White |
| 4,580,895 A | 4/1986 | Patel |

(Continued)

FOREIGN PATENT DOCUMENTS

| | | |
|---|---|---|
| WO | WO 02/26152 A1 | 4/2002 |
| WO | WO 02/40971 A1 | 5/2002 |

(Continued)

OTHER PUBLICATIONS

Communication Pursuant to Article 94(3) EPC for European Patent Application No. 07753265.3 (Apr. 12, 2012).
(Continued)

*Primary Examiner* — Vani Gupta
(74) *Attorney, Agent, or Firm* — Jenkins, Wilson, Taylor & Hunt, P.A.

(57) ABSTRACT

Systems and methods for spectral analysis of a tissue mass using an instrument, an optical probe, and a Monte Carlo algorithm or a diffusion algorithm are provided. According to one method, an instrument is inserted into a tissue mass. A fiber optic probe is applied via the instrument into the tissue mass. Turbid spectral data of the tissue mass is measured using the fiber probe. The turbid spectral data is converted to absorption, scattering, and/or intrinsic fluorescence spectral data via a Monte Carlo algorithm or diffusion algorithm. Biomarker concentrations in the tissue mass are quantified using the absorption, scattering, and/or intrinsic fluorescence spectral data.

23 Claims, 8 Drawing Sheets

Related U.S. Application Data filed on Apr. 23, 2008, provisional application No. 61/047,273, filed on Apr. 23, 2008.

(52) U.S. Cl.
CPC .......... *A61B 5/0084* (2013.01); *A61B 5/4312* (2013.01); *A61B 5/0086* (2013.01); *A61B 5/413* (2013.01)

(58) Field of Classification Search
USPC ................................................ 600/407–480
See application file for complete search history.

(56) References Cited

U.S. PATENT DOCUMENTS

| | | | |
|---|---|---|---|
| 5,125,747 | A | 6/1992 | Sayegh et al. |
| 5,186,714 | A * | 2/1993 | Boudreault et al. ............ 604/21 |
| 5,203,328 | A | 4/1993 | Samuels et al. |
| 5,439,578 | A | 8/1995 | Dovichi et al. |
| 5,452,723 | A | 9/1995 | Wu et al. |
| 5,529,391 | A | 6/1996 | Kindman et al. |
| 5,582,168 | A | 12/1996 | Samuels et al. |
| 5,792,049 | A | 8/1998 | Eppstein et al. |
| 5,813,403 | A | 9/1998 | Soller et al. |
| 5,860,421 | A | 1/1999 | Eppstein et al. |
| 5,924,981 | A | 7/1999 | Rothfritz et al. |
| 5,953,477 | A | 9/1999 | Wach et al. |
| 5,976,892 | A | 11/1999 | Bisconte |
| 5,983,125 | A | 11/1999 | Alfano et al. |
| 6,002,482 | A | 12/1999 | Rothfritz et al. |
| 6,045,502 | A | 4/2000 | Eppstein et al. |
| 6,052,177 | A | 4/2000 | Millar et al. |
| 6,055,451 | A | 4/2000 | Bambot et al. |
| 6,192,734 | B1 | 2/2001 | Rothfritz et al. |
| 6,201,989 | B1 * | 3/2001 | Whitehead ........... A61B 5/0071 250/461.2 |
| 6,219,566 | B1 | 4/2001 | Weersink et al. |
| 6,226,541 | B1 | 5/2001 | Eppstein et al. |
| 6,351,306 | B1 | 2/2002 | Tedesco et al. |
| 6,377,840 | B1 | 4/2002 | Gritsenko et al. |
| 6,400,875 | B1 | 6/2002 | Lincoln et al. |
| 6,411,373 | B1 | 6/2002 | Garside et al. |
| 6,549,284 | B1 | 4/2003 | Boas et al. |
| 6,564,088 | B1 | 5/2003 | Soller et al. |
| 6,571,118 | B1 | 5/2003 | Utzinger et al. |
| 6,577,391 | B1 | 6/2003 | Faupel et al. |
| 6,590,651 | B1 | 7/2003 | Bambot et al. |
| 6,662,030 | B2 | 12/2003 | Khalil et al. |
| 6,678,541 | B1 | 1/2004 | Durkin et al. |
| 6,813,515 | B2 | 11/2004 | Hashimshony |
| 6,825,928 | B2 | 11/2004 | Liu et al. |
| 6,850,656 | B1 | 2/2005 | Bevilacqua et al. |
| 6,870,620 | B2 | 3/2005 | Faupel et al. |
| 6,912,412 | B2 | 6/2005 | Georgakoudi et al. |
| 6,965,345 | B2 | 11/2005 | Bae et al. |
| 6,975,899 | B2 | 12/2005 | Faupel et al. |
| 7,006,220 | B2 | 2/2006 | Bambot et al. |
| 7,030,988 | B2 | 4/2006 | Kubo et al. |
| 7,062,333 | B2 | 6/2006 | Mizutani |
| 7,064,837 | B2 | 6/2006 | Mori et al. |
| 7,082,325 | B2 | 7/2006 | Hashimshony et al. |
| 7,113,624 | B2 | 9/2006 | Curry |
| 7,129,454 | B2 | 10/2006 | O'Connell et al. |
| 7,145,645 | B2 | 12/2006 | Blumenfeld et al. |
| 7,184,824 | B2 | 2/2007 | Hashimshony |
| 7,202,947 | B2 | 4/2007 | Liu et al. |
| 7,236,815 | B2 | 6/2007 | Richards-Kortum et al. |
| 7,333,189 | B2 | 2/2008 | Fulghum et al. |
| 7,382,258 | B2 | 6/2008 | Oldham et al. |
| 7,403,812 | B2 | 7/2008 | Rice et al. |
| 7,411,680 | B2 | 8/2008 | Chang et al. |
| 7,570,988 | B2 | 8/2009 | Ramanujam et al. |
| 7,751,039 | B2 | 7/2010 | Ramanujam et al. |
| 7,818,154 | B2 | 10/2010 | Palmer et al. |
| 7,835,786 | B2 | 11/2010 | Palmer et al. |
| 8,804,115 | B2 | 8/2014 | Yu et al. |
| 9,091,637 | B2 | 7/2015 | Yu et al. |
| 2002/0055671 | A1 | 5/2002 | Wu et al. |
| 2002/0114734 | A1 | 8/2002 | Pantoliano et al. |
| 2002/0193671 | A1 | 12/2002 | Ciurczak et al. |
| 2003/0016359 | A1 * | 1/2003 | Jung ........................ G01J 1/06 356/419 |
| 2003/0220549 | A1 | 11/2003 | Liu et al. |
| 2004/0010192 | A1 * | 1/2004 | Benaron et al. .............. 600/431 |
| 2004/0010375 | A1 * | 1/2004 | Schomacker et al. .......... 702/19 |
| 2004/0015062 | A1 | 1/2004 | Ntziachristos et al. |
| 2004/0064053 | A1 | 4/2004 | Chang et al. |
| 2004/0162489 | A1 | 8/2004 | Richards-Kortum et al. |
| 2004/0168692 | A1 * | 9/2004 | Fogarty et al. ............... 128/899 |
| 2004/0218172 | A1 * | 11/2004 | DeVerse et al. .............. 356/300 |
| 2004/0224315 | A1 | 11/2004 | Villa et al. |
| 2005/0030372 | A1 * | 2/2005 | Jung et al. ....................... 348/77 |
| 2005/0143663 | A1 | 6/2005 | Liu et al. |
| 2005/0162646 | A1 | 7/2005 | Tedesco et al. |
| 2005/0203419 | A1 | 9/2005 | Ramanujam et al. |
| 2005/0239197 | A1 | 10/2005 | Katerkamp et al. |
| 2006/0114457 | A1 | 6/2006 | Schmitz et al. |
| 2007/0019199 | A1 | 1/2007 | Palmer et al. |
| 2008/0056957 | A1 | 3/2008 | Hayman |
| 2008/0270091 | A1 | 10/2008 | Ramanujam et al. |
| 2009/0015826 | A1 | 1/2009 | Ramanujam et al. |
| 2009/0204009 | A1 | 8/2009 | Powers et al. |
| 2011/0059016 | A1 | 3/2011 | Ramanujam et al. |
| 2011/0105865 | A1 | 5/2011 | Yu et al. |
| 2011/0295541 | A1 | 12/2011 | Yu et al. |
| 2013/0100439 | A1 | 4/2013 | Yu et al. |

FOREIGN PATENT DOCUMENTS

| | | |
|---|---|---|
| WO | WO 2006/059226 A1 | 6/2006 |
| WO | WO 2006/076810 A1 | 7/2006 |
| WO | WO 2009/043050 A2 | 4/2009 |
| WO | WO 2009/132360 A2 | 10/2009 |
| WO | WO 2010/042249 A2 | 4/2010 |

OTHER PUBLICATIONS

Notice of Abandonment for U.S. Appl. No. 12/036,717 (dated Nov. 10, 2011).
Final Official Action for U.S. Appl. No. 12/036,717 (dated May 3, 2011).
Communication pursuant to Article 94(3) EPC for European Application No. 07 753 265.3 (dated Mar. 18, 2011).
Extended European Search Report for European Application No. 07754152.2 (dated Feb. 15, 2011).
Notice of Allowance and Fees(s) Due for U.S. Appl. No. 12/830,078 (dated Jan. 26, 2011).
Non-Final Official Action for U.S. Appl. No. 12/830,078 (dated Oct. 4, 2010).
Non-Final Official Action for U.S. Appl. No. 12/036,717 (dated Aug. 17, 2010).
Communication pursuant to Article 94(3) EPC for European Patent No. 2001352 (dated Jul. 13, 2010).
Notice of Allowance and Fee(s) Due for U.S. Appl. No. 11/493,020 (dated Jul. 6, 2010).
Notice of Allowance and Fee(s) Due for U.S. Appl. No. 11/725,141 (dated Jun. 11, 2010).
Notification of Transmittal of the International Search Report and the Written Opinion of the International Searching Authority, or the Declaration for International Application No. PCT/US2009/041732 (dated Apr. 15, 2010).
Notice of Allowance and Feed(s) Due for U.S. Appl. No. 11/493,020 (dated Mar. 10, 2010).
Extended European Search Report for European Patent No. 2001352 (dated Mar. 5, 2010).
Notice of Allowance and Fee(s) Due for U.S. Appl. No. 11/725,141 (dated Feb. 22, 2010).
Notice of Allowance and Fee(s) Due for U.S. Appl. No. 11/729,967 (dated Feb. 19, 2010).
Interview Summary for U.S. Appl. No. 11/493,020 (Nov. 17, 2009).

(56) References Cited

OTHER PUBLICATIONS

Interview Summary for U.S. Appl. No. 11/725,141 (Nov. 17, 2009).
Notice of Allowance and Fee(s) Due for U.S. Appl. No. 11/729,967 (dated Oct. 22, 2009).
Interview Summary for U.S. Appl. No. 11/729,967 (Sep. 24, 2009).
Official Action for U.S. Appl. No. 11/725,141 (dated Jun. 12, 2009).
Official Action for U.S. Appl. No. 11/729,967 (dated May 28, 2009).
Notice of Allowance and Fee(s) Due for U.S. Appl. No. 11/119,865 (dated May 1, 2009).
Office Action for U.S. Appl. No. 11/493,020 (dated Apr. 24, 2009).
Restriction and/or Election Requirement for U.S. Appl. No. 11/729,967 (Apr. 17, 2009).
Notification of Transmittal of the International Search Report and the Written Opinion of the International Searching Authority, or the Declaration for International Application No. PCT/US2008/078194 (dated Apr. 17, 2009).
Final Official Action for U.S. Appl. No. 11/119,865 (dated Mar. 18, 2009).
Notification of Transmittal of the International Search Report and the Written Opinion of the International Searching Authority, or the Declaration for International Application No. PCT/US2008/078186 (dated Feb. 17, 2009).
Restriction and/or Election Requirement for U.S. Appl. No. 11/493,020 (Feb. 10, 2009).
Communication of European Publication Number and Information on the Application of Article 67(3) EPC for European Patent No. 2005173 (dated Nov. 26, 2008).
Communication of European Publication Number and Information on the Application of Article 67(3) EPC for European Patent No. 2001352 (dated Nov. 19, 2008).
Notification of Transmittal of the International Search Report and the Written Opinion of the International Searching Authority, or the Declaration for International Application No. PCT/US07/07586 (dated Oct. 7, 2008).
Non-Final Official Action for U.S. Appl. No. 11/119,865 (dated Jul. 11, 2008).
Notification of Transmittal of the International Search Report and the Written Opinion of the International Searching Authority, or the Declaration for International Application No. PCT/US08/02431 (dated Jun. 19, 2008).
Notification of Transmittal of the International Search Report and the Written Opinion of the International Searching Authority, or the Declaration for International Application No. PCT/US06/28770 (dated Mar. 12, 2008).
Communication of European Publication Number and Information on the Application of Article 67(3) EPC for European Application No. 06800300.3 (dated Mar. 12, 2008).
Notification of Transmittal of the International Search Report and Written Opinion of the International Searching Authority, or the Declaration corresponding to PCT application No. PCT/US07/06624 (dated Feb. 7, 2008).
(Quan) Liu et al., "Experimental Proof of the Feasibility of Using an Angled Fiber-optic Probe for Depth-sensitive Fluorescence Spectroscopy of Turbid Media," Optics Letters, vol. 29, No. 17, pp. 2034-2036 (Sep. 1, 2004).
Amelink et al., "In vivo Measurement of the Local Optical Properties of Tissue by use of Differential Path-Length Spectroscopy," Optics Letters, vol. 29, No. 10, pp. 1087-1089 (May 15, 2004).
Amelink et al., "Measurement of the Local Optical Properties of Turbid Media by Differential Path-Length Spectroscopy," Applied Optics, vol. 34, No. 15, pp. 3048-3054 (May 20, 2004).
Battistelli et al., "Use of two scaling relations in the study of multiple-scattering effects on the transmittance of light beams through a turbid atmosphere," J. Opt. Soc. Am. A., vol. 2, No. 6, pp. 903-912 (Jun. 1985).
Bevilacqua et al., "In vivo local determination of tissue optical properties: applications to human brain," Applied Optics, vol. 38, No. 22, pp. 4939-4950 (Aug. 1, 1999).

Bevilacqua et al., "Monte Carlo study of diffuse reflectance at source-detector separations close to one transport mean free path," J. Opt. Soc. Am. A., vol. 16, No. 12, pp. 2935-2945 (Dec. 1999).
Bigio et al., "Spectroscopic sensing of cancer and cancer therapy: current status of translational research," Cancer Biol Ther 3(3): 259-67, (2004).
Bigio et al., "Diagnosis of breast cancer using elastic-scattering spectroscopy: preliminary clinical results," Journal of Biomedical Optics, 5(2): pp. 221-228 (2000).
Bird et al., "Metabolic Mapping of MCF10A Human Breast Cells via Multiphoton Fluorescence Lifetime Imaging Microscopy (FLIM) of the Coenzyme NADH," Cancer Research, 65(19), 8766-8773 (2005).
Biswal et al., "Recovery of Turbidity Free Fluorescence from Measured Fluorescence: An Experimental Approach," Optics Express, vol. 11, No. 24, pp. 3320-3331 (Dec. 1, 2003).
Bohnert et al.,"A Monte Carol-based Model for Steady-state Diffuse Reflectance Spectrometry in Human Skin: Estimation of Carbon Monoxide Concentration in Livor Mortis," International Journal of Legal and Medicine vol. 119, pp. 355-362 (2005).
Bolin et al., "Refractive Index of Some Mammalian Tissues Using a Fiber Optic Cladding Method," Applied Optics, vol. 28, No. 12, pp. 2297-2303 (Jun. 15, 1989).
Breslin et al., "Autofluorescence and Diffuse Reflectance Properties of Malignant and Benign Breast Tissues," Annals of Surgical Oncology, vol. 11, No. 1, pp. 65-70 (2003).
Burges, "A Tutorial on Support Vector Machines for Pattern Recognition," Data Mining and Knowledge Discovery, vol. 2, pp. 121-167 (1998).
Cerussi et al., "In vivo absorption, scattering, and physiologic properties of 58 malignant breast tumors determined by broadband diffuse optical spectroscopy," J Biomed Opt 11 :044005 (2006).
Chagpar, et al., "Intraoperative Margin Assessment Reduces Reexcision Rates in Patients with Ductal Carcinoma in Situ Treated with Breast-conserving Surgery," The American Journal of Surgery, vol. 186, pp. 371-377 (2003).
Chance et al., "Biochemical Distinctions Between Normal and Cancerous Human Breast Tissues Obtained from Fluorescence Spectroscopy," Proceedings of Optical Tomography and Spectroscopy of Tissue: Theory, Instrumentation, Model, and Human Studies II, Biomedical Optics, vol. 2979, pp. 585-588 (Feb. 9-12, 1997).
Chang et al., "Analytical Model to Describe Fluorescence Spectra of Normal and Preneoplastic Epithelial Tissue: Comparison with Monte Carlo Simulations and Clinical Measurements," Journal of Biomedical Optics, vol. 9, No. 3, pp. 511-522 (May/Jun. 2004).
Chen et al., "Approximations of Continuous Functionals by Neural Networks With Application to Dynamic Systems," IEEE on Neural Networks, vol. 4, No. 6, p. 910-918 (Nov. 1993).
Cheong et al., "A Review of the Optical Properties of Biological Tissues," Quantum Electronics, vol. 26, No. 12 (Dec. 1990).
Choe et al., "Transabdominal near infrared oximetry of hypoxic stress in fetal sheep brain in utero," Proceedings of the National Academy of Sciences, 100(22), 12950-12954 (2003).
Collier et al., "Determination of epithelial tissue scattering coefficient using confocal microscopy," IEEE J. Sel. Topics Quantum Electron. 9, 307-313 (2003).
Diamond et al., "Measurement of Fluorophore Concentrations and Fluorescence Quantum Yield in Tissue-Simulating Phantoms Using Three Diffusion Models of Steady-State Spatially Resolved Fluorescence," Physics in Medicine and Biology, vol. 48, pp. 4135-4149 (2003).
Diamond et al., "Quantification of Fluorophore Concentration in Tissue-Simulating Media by Fluorescence Measurements with a Single Optical Fiber," Applied Optics, vol. 42, No. 13, pp. 2436-2444 (May 1, 2003).
Doornbos et al., "The determination of in vivo human tissue optical properties and absolute chromophore concentrations using spatially resolved steady-state diffuse reflectance spectroscopy," Phys. Med. Biol., vol. 44, pp. 967-981 (1999).
Edge et al., "Surgical Biopsy to Diagnose Breast Cancer Adversely Affects Outcomes of Breast Cancer Care," Breast Cancer Research and Treatment, Std 01676806, vol. 94, p. S9 (2005).

(56) References Cited

OTHER PUBLICATIONS

Eiben and Smith, "Introduction to Evolutionary Computing," Springer-Verlag, Natural Computing Series, New York, New York, (2003).
Farkas et al., "Applications of spectral imaging: detection and analysis of human melanoma and its precursors," Pigment Cell Res 14(1): 2-8. (2001).
Fawzy et al., "In vivo assessment and evaluation of lung tissue morphologic and physiological changes from non-contact endoscopic reflectance spectroscopy for improving lung cancer detection," Journal of Biomedical Optics, 11(4), p. 044003 (2006).
Finlay et al., "Hemoglobin Oxygen Saturations in Phantoms and In Vivo From Measurements of Steady State Diffuse Reflectance at a Single, Short Source-detector Separation," Med Phys. vol. 31, No. 7, pp. 1949-1959 (Jul. 2004).
Fleming, et al., "Intraoperative Margin Assessment and Re-excision Rate in Breast Conserving Surgery," European Journal of Surgical Oncology, vol. 30, Issue 3, pp. 233-237 (Apr. 2004).
Gardner et al., "Fluorescence Spectroscopy of Tissue: Recovery of Intrinsic Fluorescence from Measured Fluorescence," Applied Optics, vol. 35, No. 10, pp. 1780-1792 (Apr. 1, 1996).
Gebhart et al., "Liquid-crystal tunable filter spectral imaging for brain tumor demarcation," Appl. Opt 46(10): 1896-910 (2007).
Georgakoudi et al., "NAD(P)H and Collagen as inVivo Quantitative Fluorescent Biomarkers of Epithelial Precancerous Changes," Cancer Research, vol. 62, p. 682-687 (Feb. 1, 2002).
Ghosh et al., "Measurement of Optical Transport Properties of Normal and Malignant Human Breast Tissue," Applied Optics, vol. 40, No. 1, pp. 176-184 (Jan. 1, 2001).
Graaff et al., "Condensed Monte Carlo Simulations for the Description of Light Transport," Applied Optics, vol. 32, No. 4, pp. 426-434 (Feb. 1, 1993).
Gunn, "Support Vector Machines for Classificiation and Regression," University of Southampton, Department of Electronics and Computer Science, http://homepages.cae.wisc.edu/~ece539/software/svmtoolbox/svm.pdf (May 14, 1998).
Haka et al., "In vivo margin assessment during partial mastectomy breast surgery using raman spectroscopy," Journal of Cancer Research, 66(6):3317-3322 (2006).
Hayakawa et al., "Perturbation Monte Carlo methods to solve inverse photon migration problems in heterogeneous tissues," Optics Letters, vol. 26, No. 17, pp. 1335-1337 (Sep. 1, 2001).
Kienle et al., "Spatially resolved absolute diffuse reflectance measurements for noninvasive determination of the optical scattering and absorption coefficients of biological tissue," Applied Optics, vol. 35, No. 13, pp. 2304-2314 (May 1, 1996).
Kienle et al., "Determination of the Optical Properties of Turbid Media From a Single Monte Carlo Simulation," Physics in Medicine and Biology, vol. 41, Issue 10, p. 2221-2227 (Oct. 1996).
Kuerer et al., "Lymphatic Mapping and Sentinel Lymph Node Biopsy for Breast Cancer: Developments and Resolving Controversies," Journal of Clinical Oncology, vol. 23, No. 8, pp. 1698-1705 (Mar. 10, 2005).
Laven, "Refractive index of water as a function of wavelength," http://www.philiplaven.com/p20.html, (2003).
Lee et al., "Hemoglobin measurement patterns during noninvasive diffuse optical spectroscopy monitoring of hypovolemic shock and fluid replacement," Biomed Opt 12(2): 024001, (2007).
Li et al., "Deriving the Integral Representation of a Fractional Henkel Transform From a Fractional Fourier Transform," vol. 23, No. 15, p. 1158-1160 (Aug. 1, 1998).
Lin et al., "In Vivo brain tumor demarcation using optical spectroscopy," Photochemistry and Photobiology 73(4): 396-402, (2001).
Liu et al., "Experimental Validation of Monte Carlo Modeling of Fluorescence in Tissues in the UV-Visible Spectrum," Journal of Biomedical Optics, vol. 8. No. 2, pp. 223-236 (Apr. 2003).
Liu et al., "Relationship Between Depth of a Target in a Turbid Medium and Fluorescence Measured by a Variable-Aperture Method," Optics Letters, vol. 27, Issue 2, pp. 104-106 (Jan. 15, 2002).
Liu et al., "Scaling Method for Fast Monte Carlo Simulation of Diffuse Reflectance Spectra from Multilayered Turbid Media," J. Opt. Soc. Am. A, vol. 24, No. 4, pp. 1011-1025 (Apr. 2007).
Liu et al., "Sequential Estimation of Optical Properties of a Two-layered Epithelial Tissue Model From Depth-Resolved Ultraviolet-visible Diffuse Relectance Spectra," Applied Optics, vol. 45, No. 19, pp. 4776-4790 (Jul. 1, 2006).
Lo et al., "A Strategy for Quantitative Spectral Imaging of Tissue Absorption and Scattering Using Light Emitting Diodes and Photodiodes," Optics Express, vol. 17, No. 3 (Feb. 2, 2009).
Lubawy et al., "Endoscopically compatible near infrared photon migration probe," Optics Letters, 29(17), 2022-2024 (2004).
Ma et al., "Determination of Complex Refractive Index of Polystyrene Microspheres from 370 to 1610 nm," Physics in Medicine and Biology, vol. 48, pp. 4165-4172 (2003).
Manos et al., "Optical Fiber Design Using Evolutionary Strategies," Engineering Computations, vol. 21, No. 6, pp. 564-576 (2064).
McClain et al., "Optical Absorption and Fluorescence Spectral Imaging Using Fiber Bundle Image Compression," Applied Spectroscopy, 53(9):1118-1122 (1999).
Menes, et al., "The Consequence of Multiple Re-Excisions to Obtain Clear Lumpectomy Margins in Breast Cancer Patients," Annals of Surgical Oncology, Fol. 12, No. 11, pp. 881-885 (Nov. 2005).
Merritt et al., "Coregistration of diffuse optical spectroscopy and magnetic resonance imaging in a rat tumor model," Appl. Opt. 42, 2951-2959 (Jun. 2003).
Mirabal et al., "Reflectance spectroscopy for in vivo detection of cervical precancer," J Biomed Opt 7(4): 587-94, (2002).
Morrow, et al., "Factors Predicting the Use of Breast-Conserving Therapy in Stage I and II Breast Carcinoma," Journal of Clinical Oncology, vol. 19, Issue 8, pp. 2254-2262 (Apr. 2001).
Mourant et al., "Measuring Absorption Coefficients in Small Volumes of Highly Scattering Media: Source-Detector Separations for Which Path Lengths do not Depend on Scattering Properties," Applied Optics, vol. 36, No. 22, pp. 5655-5661 (Aug. 1, 1997).
Müller et al., "Intrinsic Fluorescence Spectroscopy in Turbid Media: Disentangling Effects of Scattering and Absorption," Applied Optics, vol. 40, No. 25, pp. 4633-4646 (Sep. 1, 2001).
Nichols et al., "Design and testing of a white-light steady-state diffuse reflectance spectrometer for determination of optical properties of highly scattering systems," Appl. Opt., 36(1), pp. 93-104 (1997).
Palmer et al., "Comparison of Multiexcitation Fluorescence and Diffuse Reflectance Spectroscopy for the Diagnosis of Breast Cancer," Biomedical Engineering, vol. 50, Issue 11, pp. 1233-1242 (Nov. 2003).
Palmer et al., "Diagnosis of Breast Cancer Using Optical Spectroscopy," Medical Laser Appl. 18: 233-248 (2003).
Palmer et al., "Monte Carlo-Based Inverse Model for Calculating Tissue Optical Properties. Part I: Theory and Valdiation on Synthetic Phantoms," Applied Optics, vol. 45, No. 5, pp. 1062-1071 (Feb. 10, 2006).
Palmer et al., "Monte Carlo-Based Inverse Model for Calculating Tissue Optical Properties. Part II: Application to Breast Cancer Diagnosis," Applied Optices, vol. 45, No. 5, pp. 1072-1078 (Feb. 10, 2006).
Palmer et al., "Optimal Methods for Fluorescence and Diffuse Reflectance Measurements of Tissue Biopsy Samples," Lasers in Surgery and Medicine, vol. 30, pp. 191-200 (2002).
Palmer et al., "Auto fluorescence spectroscopy of normal and malignant human breast cells," Photochemistry and Photobiology, 78(5), 462-469 (2003).
Palmer, "Experimental, Computational, and Analytical Techniques for Diagnosing Breast Cancer Using Optical Spectroscopy," Dissertation, University of Wisconsin—Madison, pp. 1-188 (2005).

(56) References Cited

OTHER PUBLICATIONS

Pavlova et al., "Microanatomical and biochemical origins of normal and precancerous cervical autofluorescence using laser-scanning fluorescence confocal microscopy," Photochem. Photobiol. 77, 550-555 (2003).
Pfefer et al., "Influence of Illumination—Collection Geometry on Fluorescence Spectroscopy in Multilayer Tissue," Medical and Biological Engineering and Computing, vol. 42, No. 5, pp. 669-673 (Sep. 2004).
Pfefer et al., "Oblique-Incidence Illumination and Collection for Depth-Selective Fluorescence Spectroscopy," Journal of Biomedical Optics, vol. 10, No. 4, (Jul./Aug. 2005).
Pfefer et al., "Reflectance-based Determination of Optical Properties in Highly Attenuating Tissue," Journal of Biomedical Optics, vol. 8, Issue 2 (Apr. 2003).
Pfefer, et al., "Selective Detection of Fluorophore Layers in Turbid Media: The Role of Fiber-Optic Probe Design," Optics Letters, vol. 28, Issue 2, pp. 12-122 (Jan. 15, 2003).
Pogue et al., "Fiber-Optic Bundle Design for Quantitative Fluorescence Measurement From Tissue," Applied Optics, vol. 37, Issue 31, p. 7429-7436 (Nov. 1, 1998).
Prahl, "Mie Scattering Program," vol. 2003 (Copright 2007) (Downloaded from the Internet on Jan. 19, 2010).
Ramanujam, "Fluorescence Spectroscopy in Vivo," Encyclopedia of Analytical Chemistry, pp. 20-56 (2000).
Ramanujam, "Fluorescence Spectroscopy of Neoplastic and Non-Neoplastic Tissues," Neoplasia, vol. 2, Nos. 1-2, pp. 89-117 (Jan.-Apr. 2000).
Ramanujam et al., "Low temperature fluorescence imaging of freeze-trapped human cervical tissue," Opt. Exp. 8, 335-343 (2000).
Ramsay, et al., "Minimizing Local Recurrence After Breast Conserving Therapy Using Intraoperative Shaved Margins to Determine Pathologic Tumor Clearance," Journal of the American College of Surgeons, vol. 201, Issue 6, pp. 855-861 (Dec. 2005).
Sassaroli et al., "Monte Carlo procedure for investigating light propagation and imaging of highly scattering media," Applied Optics, vol. 37, No. 31, pp. 7392-7400 (Nov. 1, 1998).
Simonson et al., "Modulation of an Optical Needle's Reflectivity Alters the Average Photon Path Through Scattering Media," Journal of Biomedical Optics, vol. 11, No. 1, pp. 14-23 (Jan./Feb. 2006).
Skala et al., "Comparison of a physical model and principal component analysis for the diagnosis of normal and neoplastic epithelial tissues in vivo using diffuse reflectance spectroscopy," Optics Express 15(12): 7863-75, (2007).
Skala et al., "An Investigation of Probe Geometry Designs for the Optical Spectroscopic Diagnosis of Epithelial Pre-Cancers and Cancers," Lasers Surg Med, 34(1), 25-38 (2004).
Skala et al., "Multiphoton microscopy of endogenous fluorescence differentiates normal, pre-cancerous and cancerous squamous epithelial tissues," Cancer Research, 34, 25-38 (2005).
Stratonnikov et al., "Evaluation of blood oxygen saturation in vivo from diffuse reflectance spectra," J. Biomed Opt 6(4): 457-67, (2001).
Swartling et al., "Accelerated Monte Carlo Models to Simulate Fluorescence Spectra from Layered Tissues," Journal of Optical Society of America, vol. 20, No. 4, pp. 714-727 (Apr. 2003).
Thueler et al;., "In Vivo Endoscopic Tissue Diagnostics Based on Spectroscopic Absorption, Scattering, and Phase Function Properties," Journal of Biomedical Optics, vol. 8, No. 3, pp. 495-503 (Jul. 2003).
Tinet et al., "Fast, semianalytical Monte Carlo simulation for time-resolved light propagation in turbid media," J. Opt. Soc. Am. A., vol. 13, No. 9, pp. 1903-1915 (Sep. 1996).
Toms et al., "Intraoperative optical spectroscopy identifies infiltrating glioma margins with high sensitivity," Neurosurgery, 57(4 Suppl):382-391; discussion 382-391 (2005).
Treado et al., "Near-Infrared Acousto-optic Filtered Spectroscopic Microscopy: A Solid State Approach to Chemical Imaging," Appl. Spectrosc. 46: 553.59, (1992).
Tsenova et al., "Refractive index measurement in human tissue samples," Proc. SPIE 5226, 413-417 (2003).
Utzinger et al., "Reflectance spectroscopy for in vivo characterization of ovarian tissue," Lasers Surg Med 28(1): 56-66, (2001).
Utzinger et al., "Fiber optic probes for biomedical optical spectroscopy," J Biomed Opt, 8(1):pp. 121-147 (2003).
Van Veen et al., "Determination of visible near-IR absorption coefficients of mammalian fat using time- and spatially resolved diffuse reflectance and transmission spectroscopy," Journal of Biomedical Optics, vol. 10, No. 5, pp. 054004-1-054004-6 (Sep./Oct. 2005).
Verkruysse et al., "A library based fitting method for visual reflectance spectroscopy of human skin," Phys. Med. Biol., vol. 50, pp. 57-70 (2005).
Wall, "GAlib:Matthew Wall's Genetic Algorithm Library," vol. 2005 (2005).
Wang et al., "MCML—Monte Carlo Modeling of Light Transport in Multi-Layered Tissues," Computer Methods and Programs in Biomedicine, vol. 47, pp. 131-146 (Jul. 1995).
Wang et al., "Monte Carlo Modeling of Light Transport in Multi-Layered Tissues in Standard C," (1992).
Weersink et al., "Noninvasive Measurement of Fluorophore Concentration in Turbid Media with a Simple Fluorescence/Reflectance Ratio Technique," Applied Optics, vol. 40, No. 34, pp. 6389-6395 (Dec. 1, 2001).
Wilkinson, et al., "Concordance With Breast Cancer Pathology Reporting Practice Guidelines," Journal of the American College of Surgeons, vol. 196, Issue 1, p. 38-43 (Jan. 2003).
Wyman et al., "Similarity relations for the interaction parameters in radiation transport," Applied Optics, vol. 28, No. 24, pp. 5243-5249 (Dec. 15, 1989).
X-5 Monte Carlo Team, "MCNP—A General Monte Carlo N-Particle Transport Code, Version 5," http://mcnp-green.lanl.gov/manual.html, Los Alamos National Laboratory, pp. 1-340 (Apr. 24, 2003).
Xiaoyan et al., "Determination of Complex Refractive Index of Polystyrene Microspheres From 370 to 1610 nm," Physicis in Medicine and Biology, vol. 48, p. 4165-4172 (2003).
Yu et al., "Cost-effective Diffuse Reflectance Spectroscopy Device for Quantifying Tissue Absorption and Scattering in vivo," Journal of Biomedical Optics, vol. 13(6) (Nov./Dec. 2008).
Yu et al., "Feasability of Near-Infrared Diffuse Optical Spectroscopy on Patients Undergoing Image-Guided Core-Needle Biopsy," Optics Express 15, pp. 7335-7350 (2007).
Yu et al., "Quasi-Discrete Hankel Transform," Optical Letters, vol. 23, No. 6, pp. 409-411 (Mar. 15, 1998).
Zhang et al., "Innate Cellular Fluorescence Reflects Alterations in Cellular Proliferation," Lasers in Surgery and Medicine, vol. 20, pp. 319-331 (1997).
Zhu et al., "Diagnosis of Breast Cancer Using Diffuse Reflectance Spectroscpy: Comparison of a Monte Carlo Versus Partial Least Squares Analysis Based Feature Extraction Technique." Lasers in Surgery and Medicine, vol. 38, pp. 714-724 (2006).
Zhu et al., "Effect of Fiber Optic Probe Geometry on Depth-resolved Fluorescence Measurements From Epithelial Tissues: A Monte Carlo Simulation," Journal of Biomedical Optics, vol. 8, No. 2, p. 237-247 (Apr. 2003).
Zhu et al., "Use of a Multiseparation Fiber Optic Probe for the Optical Diagnosis of Breast Cancer," Journal of Biomedical Optics, vol. 10, No. 2, pp. 024032-1-024032-13 (Mar./Apr. 2005).
Zonios et al., "Diffuse Reflectance Spectroscopy of Human Adenomatous Colon Polyps In Vivo," Applied Optics, vol. 38, Issue 31, p. 6628-6637 (Nov. 1, 1999).
Notice of Abandonment for U.S. Appl. No. 14/531,348 (Jul. 28, 2015).
Notice of Allowance and Fee(s) Due for U.S. Appl. No. 13/513,458 (dated Mar. 17, 2015).
Notice of Abandonment for U.S. Appl. No. 12/989,595 (Dec. 26, 2014).
Commonly-assigned, co-pending U.S. Appl. No. 14/531,348 for "Diffuse Reflectance Spectroscopy Device for Quantifying Tissue Absorption and Scattering," (Unpublished, filed Nov. 3, 2014).

(56) References Cited

OTHER PUBLICATIONS

Final Office Action for U.S. Appl. No. 12/989,595 (dated Oct. 3, 2013).
Extended European Search Report for European Patent Application No. 08833169.9 (dated Jul. 11, 2013).
Extended European Search Report for European Patent Application No. 09734638.1 (dated Jul. 3, 2013).
Restriction Requirement for U.S. Appl. No. 12/680,302 (Mar. 28, 2013).
Non-Final Office Action for U.S. Appl. No. 12/989,595 (dated Mar. 20, 2013).
Communication Pursuant to Article 94(3) EPC for European Patent Application No. 07753265.3 (dated Feb. 27, 2013).
Arifler et al., "Spatially resolved reflectance spectroscopy for diagnosis of cervical precancer: Monte Carlo modeling and comparison to clinical measurements," J Biomed Opt, 11(6): p. 064027 (Nov./Dec. 2006).
Arifler et al., "Reflectance spectroscopy for diagnosis of epithelial precancer: model-based analysis of fiber-optic probe designs to resolve spectral information from epithelium and stroma," Appl Opt, 44(20): p. 4291-305 (Jul. 2005).
Bender et al., "A robust Monte Carlo model for the extraction of biological absorption and scattering in vivo," IEEE Trans Biomed Eng, 56(4): p. 960-8 (Apr. 2009).
Cardenas-Turanzas et al., "The clinical effectiveness of optical spectroscopy for the in vivo diagnosis of cervical intraepithelial neoplasia: where are we?" Gynecol Oncol, 107(1 Suppl 1): p. S138-46 (2007).
Chang et al., "Quantitative physiology of the precancerous cervix in vivo through optical spectroscopy," Neoplasia, 11(4): p. 325-32 (Apr. 2009).
Chang et al., "Combined reflectance and fluorescence spectroscopy for in vivo detection of cervical pre-cancer," J Biomed Opt, 10(2): p. 024031 (Mar./Apr. 2005).
Freeberg et al., "The performance of fluorescence and reflectance spectroscopy for the in vivo diagnosis of cervical neoplasia; point probe versus multispectral approaches," Gynecol Oncol, 107(1 Suppl 1): p. S248-55.
Georgakoudi et al., "Trimodal spectroscopy for the detection and characterization of cervical precancers in vivo," Am J Obstet Gynecol, 186(3): p. 374-82 (2002).
Liu et al., "Experimental proof of the feasibility of using an angled fiber-optic probe for depth-sensitive fluorescence spectroscopy of turbid media," Opt Lett, 29(17): p. 2034-6 (Sep. 2004).
Marin et al., "Diffuse reflectance patterns in cervical spectroscopy," Gynecol Oncol, 99(3 Suppl 1): p. S116-20 (2005).
Pavlova et al., "Fluorescence spectroscopy of oral tissue: Monte Carlo modeling with site-specific tissue properties," J Biomed Opt, 14(1): p. 014009 (Jan./Feb. 2009).
Reif et al., "Analysis of changes in reflectance measurements on biological tissues subjected to different probe pressures," J Biomed Opt, 13(1): p. 010502 (Jan./Feb. 2008).
Schwarz et al., "Autofluorescence and diffuse reflectance spectroscopy of oral epithelial tissue using a depth-sensitive fiber-optic probe," Appl Opt, 47(6): p. 825-34 (Feb. 2008).
de Veld et al., "Autofluorescence and diffuse reflectance spectroscopy for oral oncology," Lasers Surg Med, 36(5): p. 356-64 (2005).
Yu et al., "Diffuse reflectance spectroscopy with a self-calibrating fiber optic probe," Opt Lett, 33(16): p. 1783-85 (2008).
Communication under Rule 71(3) EPC for European Patent Application No. 07753265.3 (dated Sep. 16, 2014).
Non-Final Office Action for U.S. Appl. No. 13/513,458 (dated Aug. 28, 2014).
Corrected Notice of Allowability for U.S. Appl. No. 12/989,591 (dated Jul. 17, 2014).
Notice of Allowance and Fee(s) Due for U.S. Appl. No. 12/989,591 (dated Feb. 11, 2014).

\* cited by examiner

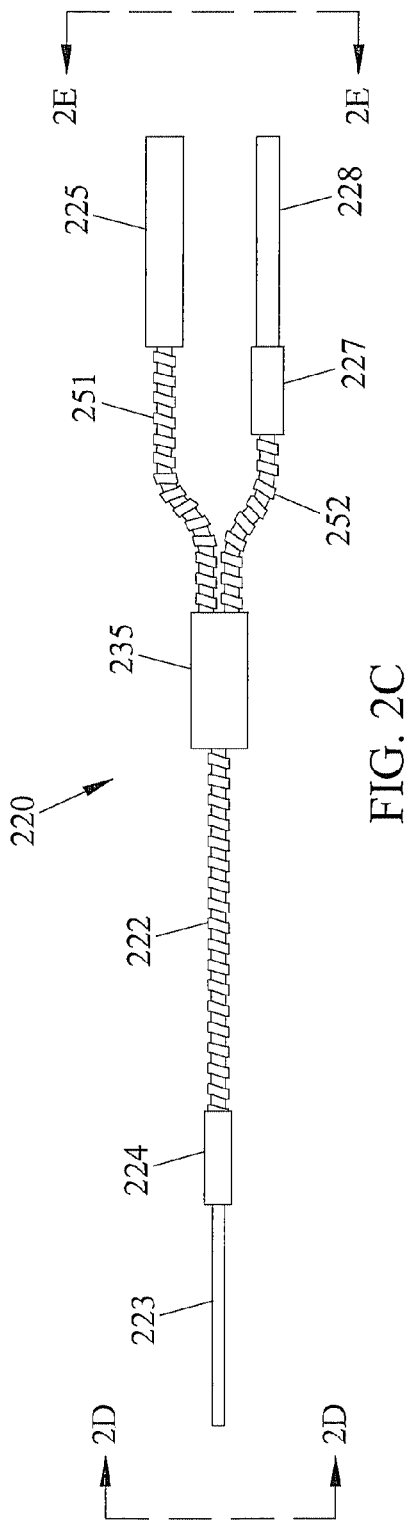
FIG. 2C
FIG. 2E
FIG. 2D

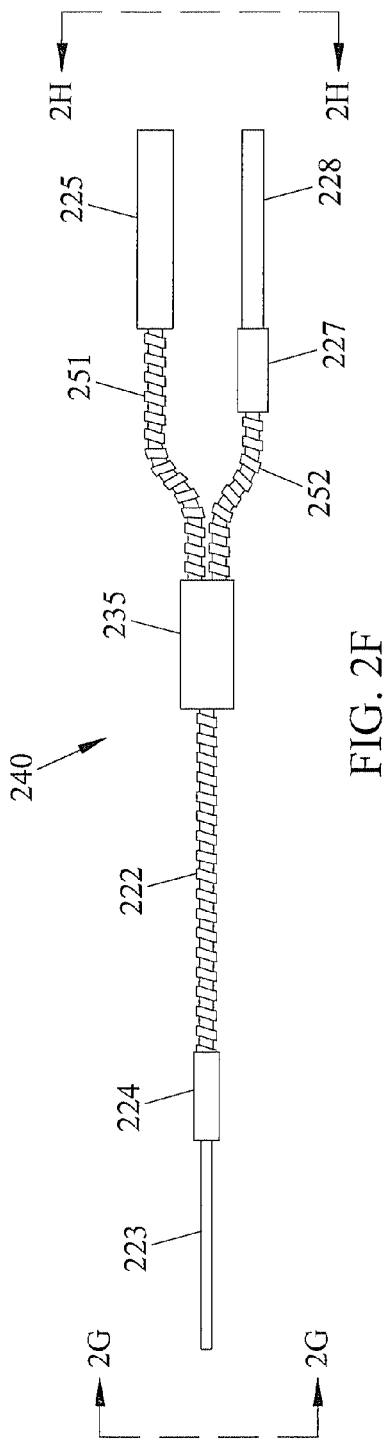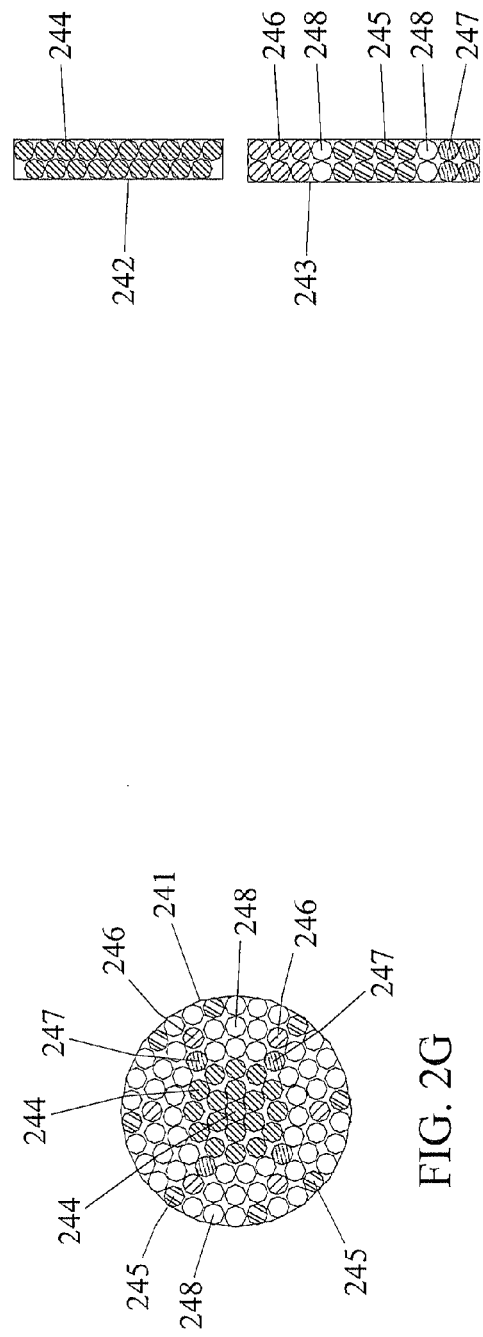
FIG. 2F
FIG. 2G
FIG. 2H

SYSTEMS AND METHODS FOR SPECTRAL ANALYSIS OF A TISSUE MASS USING AN INSTRUMENT, AN OPTICAL PROBE, AND A MONTE CARLO OR A DIFFUSION ALGORITHM

RELATED APPLICATIONS

This application claims the benefit of U.S. Provisional Patent Application Ser. No. 60/995,826, filed Sep. 28, 2007, U.S. Provisional Patent Application Ser. No. 61/047,273, filed Apr. 23, 2008, and U.S. Provisional Patent Application Ser. No. 61/047,270, filed Apr. 23, 2008; the disclosure of each of which is incorporated herein by reference in its entirety.

GOVERNMENT INTEREST

This presently disclosed subject matter was made with U.S. Government support under Grant No. 1R01CA100559 awarded by NIH. Thus, the U.S. Government has certain rights in the presently disclosed subject matter.

TECHNICAL FIELD

The subject matter disclosed herein relates to optical spectroscopy and tissue physiology. More particularly, the subject matter disclosed herein relates to systems and methods for using a fiber optic probe to determine biomarker concentrations in a tissue mass.

BACKGROUND

Presently, optical spectroscopy may be used in some applications to serve as a diagnostic tool to detect various diseases. Notably, optical spectroscopy is sensitive to a number of biological scatterers, absorbers and fluorophores that exist in tissue. Absorbers include hemoglobin, adipose, water, beta carotene and melanin and other proteins. Scatterers include cellular and subcellular organelles. Fluorophores include metabolic electron carriers and structural proteins. Namely, these biological scatterers, absorbers, and fluorophores may be used to indicate the existence of certain diseases. Optical spectroscopy can therefore be used to provide early diagnosis of diseases, such as Alzheimer's disease, cardiovascular disease, breast cancer, and the like. The use of such technology for early detection of diseases is invaluable. For example, each year in the United States, numerous women are diagnosed with breast cancer. While this disease takes many lives, the likelihood of survival is greatly increased with early treatment of abnormalities that are discovered via breast examinations and mammograms.

In the field of breast cancer diagnosis, current methods for determining whether an abnormality is cancerous include performing an open surgical biopsy or a needle biopsy. Of the two, needle biopsy is less invasive, faster, less expensive, and requires a shorter recovery time. However, there are drawbacks to the needle biopsy procedure due to the limited sampling accuracy associated with the technique. Because only a few samples of tissue are taken from the abnormality, the possibility that a biopsy will either provide a false negative or will be inconclusive (and require a repeat biopsy) exists.

One solution to overcome these shortcomings is to utilize optical spectroscopy to probe the abnormality. Namely, research has been conducted that indicates that ultra violet-visible-near infrared (UV-VIS-NIR) spectroscopic methods show distinct differences between the spectra of normal, benign, and malignant tissues. For example, various fluorescence studies have investigated the fluorescence emission and excitation spectra to differentiate malignant tissue from benign and some normal tissue in the breast. Other studies have used fluorescence to strictly differentiate between malignant and normal fibrous tissues. While fluorescence has been used to identify several types of breast tissue, it is difficult to distinguish malignant tissues from benign tissues using fluorescence alone.

One way to compensate for the deficiency in fluorescence techniques is to use diffuse reflectance spectroscopy. Diffuse reflectance spectroscopy (e.g., visible (400-600 nm) and VIS-NIR (650-1000 nm)) takes advantage of the non-fluorescent absorbers and scatterers in breast tissue to distinguish between benign tissues and malignant tissues. Past studies have demonstrated that diffuse reflectance spectra can be measured during breast cancer surgery to identify malignant and normal tissues.

Recently, researchers have investigated the use of fluorescence spectra and diffuse reflectance spectra in combination to diagnose breast cancer ex vivo. From these studies, researchers discovered that the diffuse reflectance spectra coupled with the fluorescence emission spectra provided for distinguishing between malignant and nonmalignant tissues. Additionally, other studies have utilized a fiber optic probe to take fluorescence and diffuse reflectance spectra for the investigation of ex vivo breast tissue samples.

Despite the advances in the area of optical spectroscopy, there still remains a need for an effective method and apparatus for an in vivo optical probe that combines fluorescence and diffuse reflectance spectroscopy to improve biopsy procedures. Difficulties involved with providing an optical probe access to the tumor, form factor considerations, and the like have presented problems that hinder the implementation of such medical devices or methods. These difficulties may also present obstacles for other applications of optical spectroscopy in the medical arena, such as diagnostic monitoring, therapeutic monitoring, drug discovery and analysis, tissue oxygenation monitoring in surgical procedures, and the like.

Thus, there remains a need for an improved system and method for conducting spectral analysis of a tissue mass using an insertable instrument, an optical probe, and a Monte Carlo or diffusion algorithm.

SUMMARY

The subject matter described herein includes systems and methods for spectral analysis of a tissue mass using an instrument (such as a biopsy needle, an endoscope, or a catheter), an optical probe, a Monte Carlo algorithm or a diffusion algorithm. According to one aspect, an instrument, such as a biopsy needle is inserted into a tissue mass. A fiber optic probe is applied via the instrument into the tissue mass. Turbid spectral data of the tissue mass is measured using the fiber optic probe. The turbid spectral data is converted to absorption, scattering, and/or intrinsic fluorescence spectral data via a Monte Carlo algorithm or a diffusion algorithm. Biomarker concentrations in the tissue mass are quantified using the absorption, scattering, and/or intrinsic fluorescence spectral data. In an alternate embodiment, where the tissue is visible, the optical probe may be placed directly on the mass without the aid of an instrument.

BRIEF DESCRIPTION OF THE DRAWINGS

Preferred embodiments of the subject matter described herein will now be described with reference to the accompanying drawings, of which:

FIG. 2C is a diagram of an exemplary forward firing fiber optic probe with a single collection ring that is interfaced with a tissue mass according to an embodiment of the subject matter described herein;

FIG. 2D is a diagram of an exemplary probe tip of a forward firing fiber optic probe with a single collection ring according to an embodiment of the subject matter described herein;

FIG. 2E is a diagram of vertical fiber arrays positioned at the termini of a forward firing fiber optic probe with a single collection ring according to an embodiment of the subject matter described herein;

FIG. 2F is a diagram of an exemplary forward firing fiber optic probe with multiple collection rings that is interfaced with a tissue mass according to an embodiment of the subject matter described herein;

FIG. 2G is a diagram of an exemplary probe tip of a forward firing fiber optic probe with multiple collection rings according to an embodiment of the subject matter described herein;

FIG. 2H is a diagram of vertical fiber arrays positioned at the termini of a forward firing fiber optic probe with multiple collection rings according to an embodiment of the subject matter described herein;

DETAILED DESCRIPTION

Figure 1:
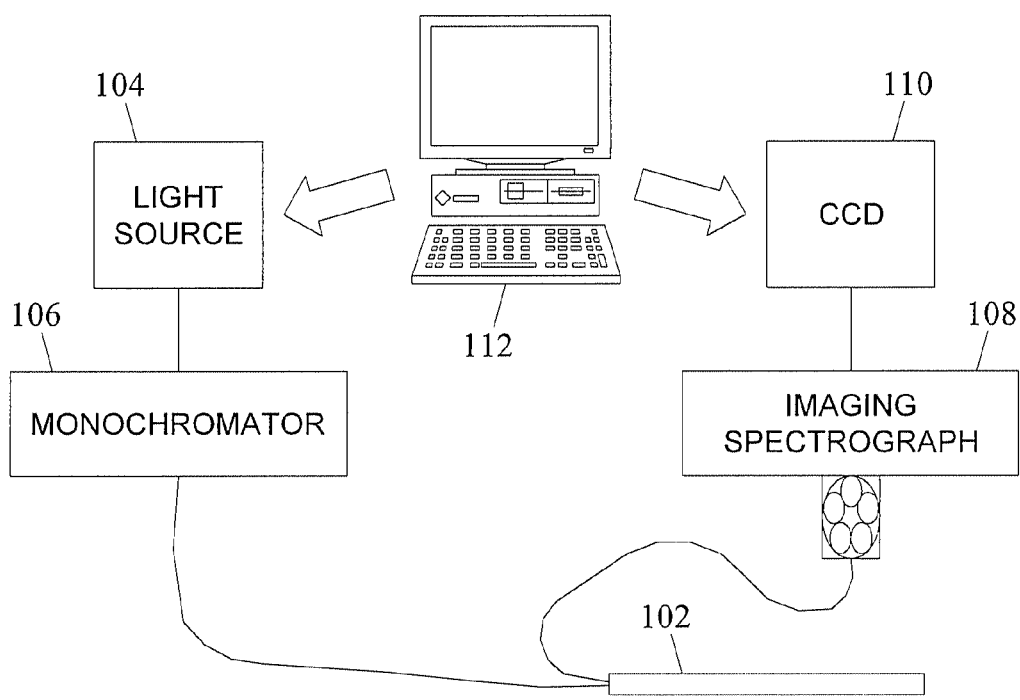
FIG. 1 is a block diagram of an optical spectrometer system for determining biomarker concentrations in a tissue mass according to an embodiment of the subject matter described herein.

The subject matter described herein includes systems and methods for spectral analysis of a tissue mass using an instrument, an optical probe, and a Monte Carlo algorithm or a diffusion algorithm. According to one aspect, a fiber optic probe may be used to measure biomarkers in a tissue mass. As used herein, biomarkers may be defined as quantifiable components naturally found associated with tissue, and include, but are not limited to, oxygenated and deoxygenated hemoglobin, adipose, protein, beta carotene, myoglobin, nicotinamide adenine dinucleotide (NADH), nicotinamide adenine dinucleotide phosphate (NADPH), flavin adenine dinucleotide (FAD), and collagen. Other biomarkers may include blood volume, drug uptake, lipid content, water content. Redox ratio, cytochrome oxidase (CtOx), drug uptake, and contrast agent uptake in the tissue mass. Notably, biomarkers can be utilized to monitor physiological conditions in a human subject or patient since changes in biomarker concentrations may serve as an indicator of tissue disease. For example, cancer may be detected by an increase in blood vessel growth and a decrease in blood oxygenation, both of which may be indicated by changes in certain biomarker concentrations, such as oxygenated and deoxygenated hemoglobin.

In one embodiment of the present subject matter, biomarkers may be measured by taking optical measurements with a fiber optic probe. For example, a fiber optic probe must initially interface (e.g., placed in contact) with a tissue mass to be analyzed. If the measurement is to be conducted ex vivo, there are relatively few difficulties involved with the acquisition of the optical measurements needed to yield biomarker concentrations. For example, if a tissue mass (e.g., a tumor) is visible, an insertable instrument may not be required since the fiber optic probe may be placed directly on the tissue mass. Alternatively, if the optical measurement is to be made in vivo, then additional steps may be taken to position the probe in contact with the internal tissue mass or surrounding biopsy site.

In one embodiment, for in vivo spectral measurements, a small incision may be made into the skin (e.g., by a cutting needle) to accommodate an instrument. Exemplary instruments include, but are not limited to, biopsy needles, cannulas, endoscopic instruments, laparoscopic instruments, or any combination thereof. For example, the instrument, such as a biopsy needle-cannula device (e.g., a Bard Vacora 10 G or 14 G biopsy needle and coaxial cannula or a Cardinal Achieve 14 G biopsy needle and coaxial cannula) may be inserted through the incision and guided via ultrasound to the tissue site of interest. The biopsy needle is subsequently extracted, thus leaving the cannula in place and in contact with the tissue site. A fiber optic probe (e.g., a forward firing fiber optic probe) is then inserted through the hollow cannula to interface with the tissue site. Once in contact with the tissue mass, the probe is used to take optical measurements, which are interpreted by an algorithm (executed by a processor) that yields biomarker concentrations. A biopsy needle may then be used to remove a tissue sample. In embodiments that specifically use a side firing fiber optic probe, the probe is adapted to fit within the biopsy needle (e.g., a Suros 9 G or Mammotome biopsy needle) itself. For example, a side-firing fiber optic probe may be directly inserted into the bore of the biopsy needle and aligned to the side aperture on the biopsy needle.

In one embodiment, the optical measurements include turbid spectral data, such as reflectance spectral data and fluorescence spectral data. The fiber optic probe is ultimately retracted so a biopsy of interrogated tissue may be made through the cannula if necessary.

In one embodiment, an optical spectrometer system may be used to obtain optical measurements via a fiber optic probe and process the measurement data in order to yield biomarker concentrations. FIG. 1A depicts an exemplary optical spectrometer system 100 that includes a fiber optic probe 102. Spectrometer system 100 may also include a light source 104 (e.g., a xenon lamp), a monochromator 106 (e.g., a scanning double-excitation monochromator), an imaging spectrograph 108, a charged-couple device (CCD) unit 110, and a processing unit 112 (e.g., a computer).

In one aspect of the present subject matter, fiber optic probe 102 may be adapted to fit any instrument. Possible probe adaptations include, but are not limited to, side firing probes and forward firing probes. One embodiment of probe 102 may be found in Zhu et al., "Use of a multiseparation fiber optic probe for the optical diagnosis of breast cancer," *Journal of Biomedical Optics* 10(2), 024032 (March/April 2005). Other exemplary embodiments of fiber optic probes are shown below in FIGS. 2B, 2C, and 2F.

Probe geometry can be optimized for measurement of spectroscopic data in turbid media. Optimizing probe geometry may include selecting the numbers and geometry of collection and illumination fibers. One exemplary method for optimizing probe geometry is found in U.S. patent application publication number 2007/0019199 to Palmer et al., the disclosure of which is hereby incorporated herein by reference in its entirety. For example, the probe geometry to be optimized may include at least one emitting probe fiber for emitting electromagnetic radiation into a turbid medium and at least one collecting probe fiber for collecting the electromagnetic radiation that has interacted with the turbid medium. A simulation may be performed with inputs of the probe geometry and a plurality of sets of optical property values associated with the turbid medium to generate output comprising optical parameter values measured by the probe geometry for each set of input optical property values. The measured optical parameter values are input to an inversion algorithm to produce corresponding optical properties as output. The produced optical properties are compared with optical properties known to correspond to the measured optical parameter values and a degree of matching between the produced optical properties and the known optical properties is determined. The simulation and inversion steps are repeated for a plurality of additional probe geometries. Each additional probe geometry differs from the previously tested probe geometry in at least one property. For example, the property may be a quantity of collecting entities, a diameter of at least one emitting or collecting entity, a linear distance between the emitting and collecting entities, or combinations thereof. An optimization algorithm is applied at each iteration to select a probe geometry such that the resulting degree of matching will converge to an optimum value. An optimal geometry is selected based on the degree of matching determined for each geometry.

The aforementioned inversion algorithm used to interpret the turbid spectral data may extract the optical properties from the probe measurements. In one embodiment, the algorithm may include a Monte Carlo algorithm that is executed by processing unit 112. Similarly, the Monte Carlo algorithm may also include an inverse Monte Carlo reflectance algorithm or an inverse Monte Carlo fluorescence algorithm. An exemplary Monte Carlo algorithm suitable for use with the subject matter described herein is found in international patent application number PCT/US2007/006624 to Palmer and Ramanujam and U.S. patent application publication 2006/0247532 to Ramanujam et al. An exemplary scaling method for expediting calculations performed in the Monte Carlo algorithm is described in U.S. provisional patent application Ser. No. 60/903,177, filed Feb. 23, 2007.

As mentioned above, fiber optic probe measurements may include optical spectra data. Possible probe measurements include, but are not limited to, measuring the turbid spectral data, such as fluorescence and diffuse reflectance spectra. Diffuse reflectance may be used to measure only the absorption and scattering properties in tissue. Fluorescence spectra data may be obtained by applying excitation light to the tissue sample in order to measure the intrinsic fluorescence emission properties of biomarkers, corrected for the absorption and scattering properties in tissue. One embodiment may utilize fluorescence excitation and emission spectra, as well as diffuse reflectance spectra, in the ultraviolet and visible (UV-VIS) range. For example, a probe capable of measuring the fluorescent spectra with excitation wavelengths ranging from 300-460 nm and diffuse reflectance spectra measured from 300-800 nm may be used to detect cancer.

Additionally, more optimal measurements may be taken if the spectral resolution of the spectrometer collecting the reflectance data (e.g., imaging spectrograph 108 in FIG. 1A) is narrower than the narrowest spectral band being investigated. In one embodiment a spectral resolution that is at least a factor of two narrower than the narrowest spectral band may be used. For evaluating biological tissue, a spectrometer with a spectral bandpass of between about 2.5 nm and about 5 nm may be utilized.

Figure 2A:
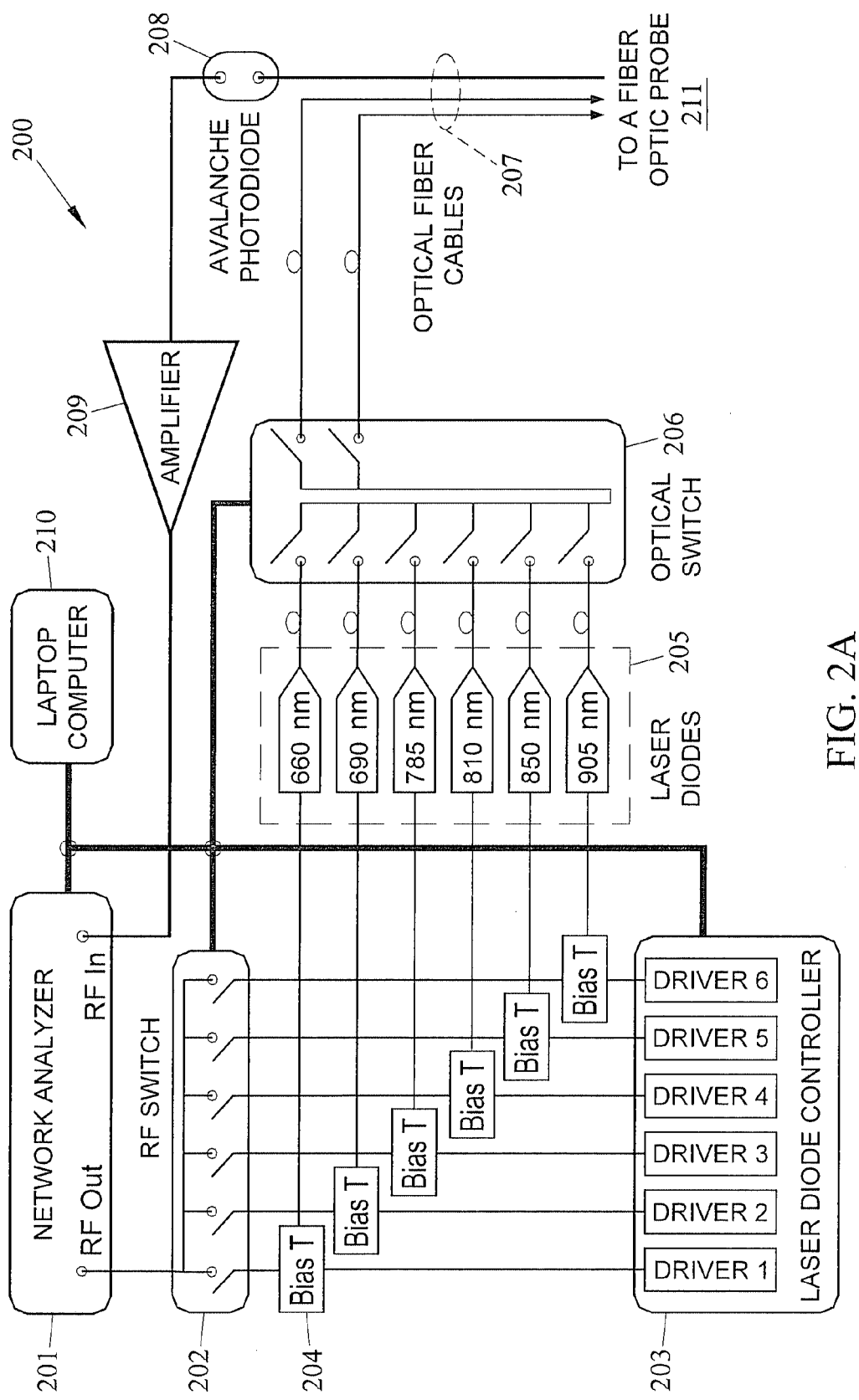
FIG. 2A is a block diagram of an exemplary frequency-domain near-infrared spectrometer for determining biomarker concentrations in a tissue mass according to an embodiment of the subject matter described herein.
Figure 2B:
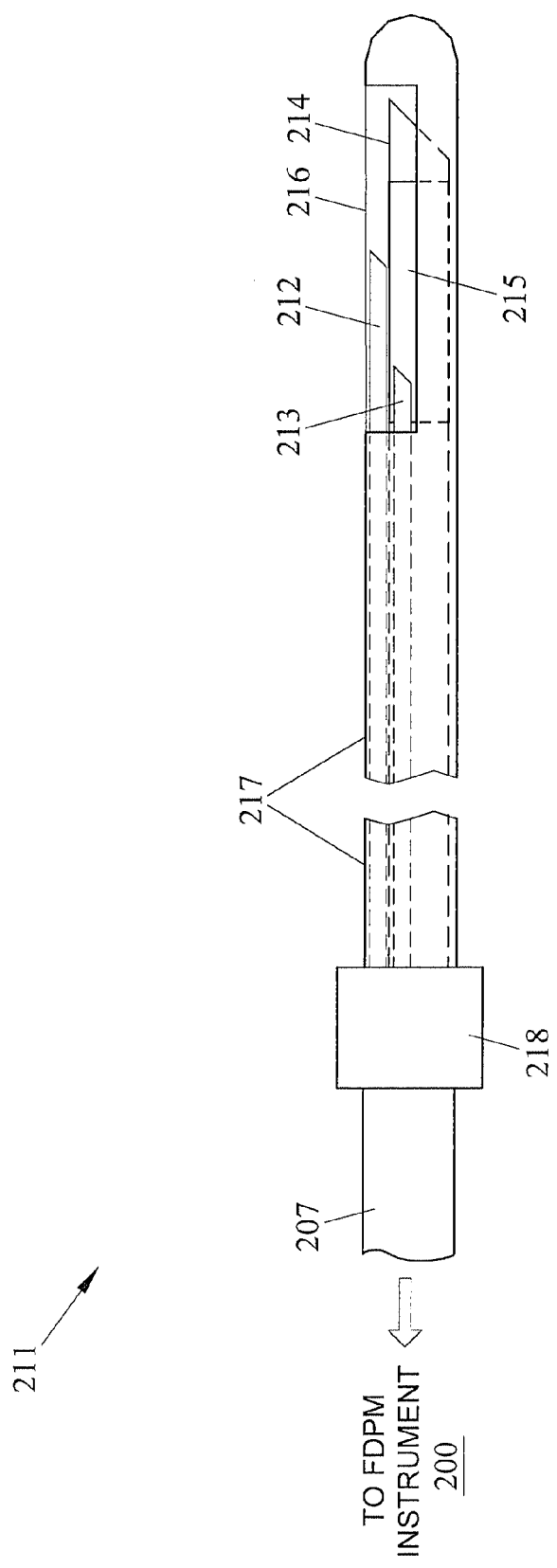
FIG. 2B is a diagram of an exemplary side firing fiber optic probe that is interfaced with a tissue mass according to an embodiment of the subject matter described herein.

In another embodiment, a frequency-domain near-infrared optical spectrometer system may be used to obtain optical measurements via a side firing fiber optic probe and process the measurement data in order to yield biomarker concentrations. FIG. 2A depicts an exemplary frequency-domain near-infrared optical spectrometer system 200 and FIG. 2B depicts an exemplary side firing fiber optic probe 211 to be used with the spectrometer system 200. System 200 may include a network analyzer 201, a radio frequency (RF) switch 202, a laser diode controller 203, six bias T's 204, six laser diodes 205, an optical switch 206, optical fiber cable 207 interfacing a fiber optic probe 211, an avalanche photodiode (APD) 208, a broadband amplifier 209, and a laptop computer 210. In one embodiment, network analyzer 201 may be replaced by a RF source with a sweep range from 50-500 MHz and a lock-in amplifier. Similarly, possible probe adaptations include, but are not limited to, side firing probes and forward firing probes. One embodiment of probe 211 may be found in U.S. patent application publication number 2005/0203419 to Ramanujam et al. In one embodiment, the frequency-domain near-infrared optical spectrometer system 200 may comprise a frequency domain photon migration (FDPM) instrument when a side firing probe is used.

FIG. 2B shows a diagram of an exemplary side firing fiber optic probe 211 that interfaces with a tissue mass (e.g., a tumor). In one embodiment, probe 211 has an outer diameter of 1 to 3 mm that includes two side firing illumination fibers 212 and 213, and a side firing collection fiber 214, all inside an end-sealed stainless steel tube 217. Notably, the two side firing illumination fibers and side firing collection fiber forms two source-detector separations, wherein, each of the source-detector separations range between 3 to 15 millimeters. In one embodiment, the side firing fiber optic probe uses the illumination fibers and collection fiber to achieve a sensing depth (i.e., depth of tissue which may be inspected) ranging from 0.5 to 10 millimeters. Steel tube 217 may include a side aperture a few millimeters from the sealed end, from which diffuse reflectance measurements can be made. The tips of fibers 212, 213 and 214 are polished to a 45 degree angle and are coated with a reflective film. An absorptive coating 215 is applied on the outer surface of collection fiber 214 a few millimeters (e.g., 2-3 mm) away from the angle fiber tip to prevent any light from leaking directly from illumination fibers 212 and 213 into collection fiber 214. A thin layer of biocompatible optical epoxy 216 can be used to seal the aperture on the stainless steel tube 217 and to protect the fibers from any scratch. An adaptor 218 can be used to align probe 211 to an instrument, such as a biopsy core needle. Fiber optic cable 207 interfaces probe 211 to spectrometer 200 (see FIG. 2A). In one embodiment, the side firing fiber optic probe may be adapted for inserting into the tissue mass in order to measure turbid spectral data of the tissue mass. For example, the sealed end of the side firing fiber optic probe may be sharpened to be used as a needle for insertion into the tissue mass.

FIG. 2C depicts a diagram of an exemplary forward firing fiber optic probe 220 including a single collection ring that may be interfaced with a tissue mass. In one embodiment, forward firing fiber optic probe 220 comprises a flexible steel sheathed tubing that contains a plurality of optical fibers. Fiber optic probe includes a portion 222 that comprises a rigid probe tip 223 on one end and a breakout tube 235 on the opposite end. Breakout tube 235 allows for the bifurcation of portion 222 into two different optical fiber groupings (e.g., an illumination fiber "leg" 251 and a collection fiber "leg" 252). Fiber optic probe 220 may also include rigid members 224-228 (e.g., t-tubes and ferrules) that provide stability and interfacing capability for fiber optic probe 220. Probe tip 223 may include a plurality of fibers arranged in a configuration as shown in pattern 221 (see FIG. 2D), which comprises 19 illumination fibers 230 centrally grouped to form an illumination core. Although 19 illumination fibers are depicted in FIG. 2D, any number of fibers may be used. For example, the illumination core may include any number of fibers to obtain an illumination core diameter that maximizes the coupling efficiency for the light source, and the (signal-to-noise ration) SNR for the fluorescence measurements. As shown in FIG. 2D, the illumination core may also be surrounded by a single ring of collection fibers 231. In one embodiment, the illumination fibers are used to emit light on the tissue sample to be examined. The light may be generated by light source 104 and provided to fiber optic probe 220 via monochromator 106. Specifically, light is emitted into one end of illumination fibers 230 (i.e., into vertical illumination fiber array 226, which is located on the open-ended terminus of ferrule 225). Fiber array 226 (shown in FIG. 2E) is one possible arrangement in which the fibers can be coupled to monochromator 106. Notably, each end of illumination fiber 230 in fiber array 226 corresponds to a terminus of illumination fiber 230 in probe tip 223 (i.e., each individual optical fiber runs the entire length of probe 220). After the light is emitted by the illumination fibers 230 on a tissue mass, at least one collection fiber 231 captures the reflected light which is ultimately provided to imaging spectrograph 108 (via the interface created by fiber array 229 which is located on the open-ended terminus of ferrule 228 as shown in FIG. 2E). In one embodiment, probe tip 223 is 9.3 cm long and has a diameter of 2.1 mm in order to fit within the lumen of a 14 gauge biopsy needle cannula. In one embodiment, forward firing fiber optic probe 220 uses the illumination fibers and collection fibers to achieve a sensing depth (i.e., depth of tissue which may be inspected) ranging from 0.5 to 10 millimeters.

FIG. 2F depicts a diagram of an exemplary forward firing fiber optic probe 240 with multiple collection rings that may be interfaced with a tissue mass. In one embodiment, forward firing fiber optic probe 240 may be nearly identical to fiber optic probe 220 in FIG. 2C with the exception of the diameter of probe tip 223, the arrangement of fibers in pattern 241 (see FIG. 2G), and the number and types of fibers contained in fiber array 249 (see FIG. 2H). For example, probe tip 223 may be configured to include 19 illumination fibers centrally grouped and surrounded by three concentric layers of fibers (i.e., collection rings). Each collection ring includes a plurality of dead fibers and a plurality of live collection fibers, wherein each of the collection fibers may be distinguished by its collection ring placement. In other words, collection fibers located in the outermost collection ring are distinguished (i.e., for data collection purposes) from the collection fibers positioned in the innermost collection ring. The dead fibers 248 may be the same size as illumination fibers 244 and live collection fibers 245 for the purpose of bundle packing. The output signals from the three concentric rings of collection fibers are spatially separated by CCD unit 110 (see FIG. 1A), thereby enabling fluorescence and diffuse reflectance spectra to be measured at three illumination-collection separations simultaneously. As shown in FIG. 2G, the outermost collection ring comprising 8 outer layer collection fibers 245 interspersed among and separated by 22 dead fibers 248. Similarly, the middle collection ring includes 6 middle layer collection fibers 246 interspersed among and separated by 18 dead fibers 248. Lastly, the innermost collection ring includes 4 inner layer collection fibers 247 interspersed among and separated by 15 dead fibers 248. One advantage of arranging the collection fibers in this manner is that fiber optic probe 240 is capable of taking measurements at three different sensing depths within the tissue mass. In one embodiment, the probe tip 223 is 9.3 cm long and has a diameter of 3.4 mm in order to fit within the lumen of a 10 gauge biopsy needle cannula. In one embodiment, forward firing fiber optic probe 240 uses the illumination fibers and collection fibers to achieve a sensing depth (i.e., depth of tissue which may be inspected) ranging from 0.5 to 10 millimeters.

Figure 3:
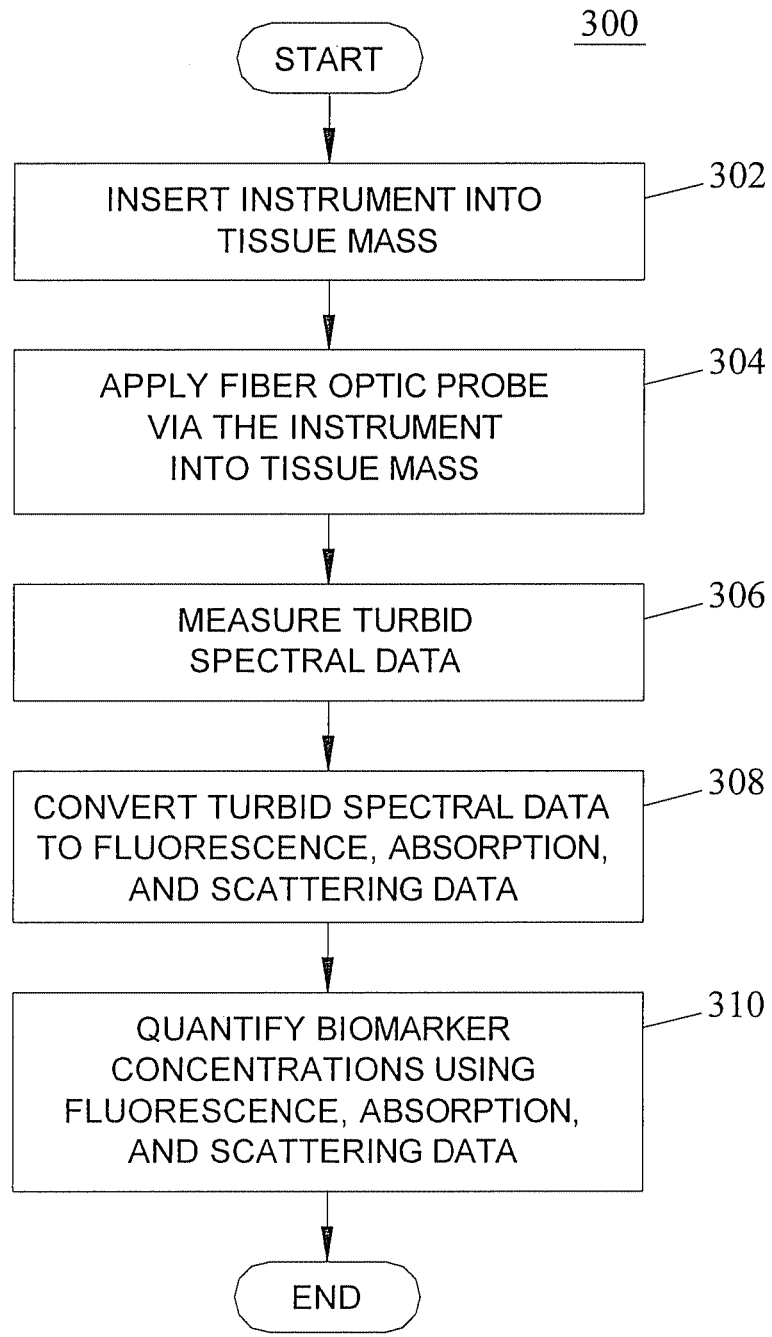
FIG. 3 is a flow chart of an exemplary process for quantifying biomarker concentrations according to an embodiment of the subject matter described herein.

FIG. 3 is a flow diagram illustrating the steps of an exemplary method 300 for determining biomarker concentrations in a tissue mass according to an embodiment of the subject matter described herein. Referring to FIG. 3, in block 302, an instrument is inserted in a tissue mass. In one embodiment, a biopsy needle-cannula instrument is inserted into or interfaces a tissue mass, such as a tumor, using ultrasound for guidance.

In block 304, a fiber optic probe is applied into the tissue mass via the instrument. In one embodiment, the needle is first retracted from the cannula (i.e., the hollow cannula remains in the tumor while the biopsy needle is withdrawn) and is subsequently replaced by fiber optic probe 102 (see FIG. 1). Essentially, fiber optic probe 102 uses the cannula as a guide to access the tumor. It is appreciated that fiber optic probe 102 may be placed in proximity, in contact, or within the tumor depending on the particular application. In another embodiment, a biopsy core needle is first fired into a tissue mass with guidance from mammography or ultrasound and the cutter in the needle is retracted such that the side-facing aperture on the needle is open. Then side firing fiber optic probe 211 may be inserted into the needle and oriented to face the aperture and diffuse reflectance spectroscopy measurements are made from the tissue site adjacent to the side facing aperture. In an alternate embodiment, an insertable instrument may not be required if the tissue mass is visible. Rather the fiber optic probe may be applied directly to the tissue mass.

In block 306, turbid spectral data is measured. In one embodiment, turbid spectral data is measured using fiber optic probe 102. For example, fiber optic probe 102 may be used to make optical measurements, such as fluorescence spectra measurements and diffuse reflectance measurements, of the tumor. In another embodiment, turbid spectral data is measured using fiber optic probe 211. For example, fiber optic probe 211 may be used to make optical measurements, such as diffuse reflectance measurements, of the tumor.

In block 308, the turbid spectral data is converted to absorption, scattering, and/or intrinsic fluorescence data. In one embodiment, the measured turbid spectral data is used as input for a Monte Carlo algorithm. Using the turbid spectral data and the Monte Carlo algorithm, a processing unit (e.g., processing unit 112 in FIG. 1) may convert the data into absorption, scattering, and intrinsic fluorescence data that can be easily interpreted and analyzed. In another embodiment, the measured turbid spectral data is used as input for a diffusion algorithm, a processing unit (e.g., laptop computer 210 in FIG. 2A) may convert the data into absorption and scattering data that can be interpreted and analyzed. An exemplary diffusion algorithm can be found in Yu et. al. "*Feasibility of near-infrared diffuse optical spectroscopy on patients undergoing image-guided core-needle biopsy,*" *Optics Express* 15, 7335-7350 (2007).

In block 310, biomarker concentrations are quantified using the combined spectral data (i.e., absorption, scattering, and/or intrinsic fluorescence data). In one embodiment, the combined spectral data may be analyzed and processed to quantify the biomarker concentrations existing in the tissue mass (i.e., the tumor). Once the biomarker concentrations are quantified, specific physiological conditions can be determined. Method 300 then ends.

Figure 4:
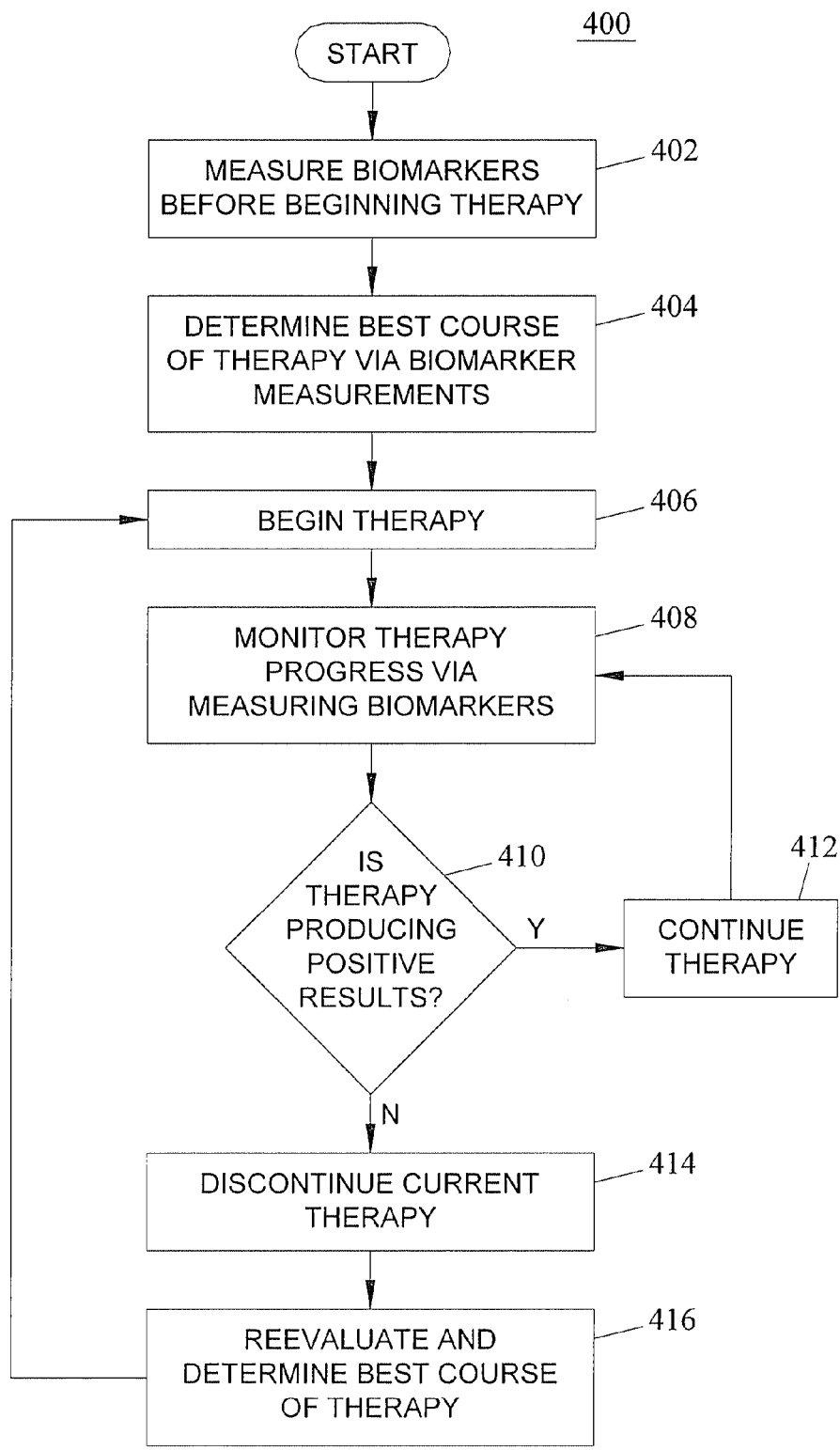
FIG. 4 is a flow chart of an exemplary process for measuring biomarker concentrations for therapeutic applications according to an embodiment of the subject matter described herein.

Although FIG. 3 describes a general method for determining biomarker concentrations, it is appreciated that method 300 may be modified for specific medical applications. For example, FIG. 4 depicts an exemplary method 400 for determining biomarker concentrations in order to provide therapeutic screening. Referring to FIG. 3, in block 402, known biomarkers are measured. In one embodiment, known biomarkers of cancer may be measured by using an instrument that positions a fiber optic probe 102 or 211 on a tissue mass, such as a tumor, in vivo. Probe 102 or 211 may then obtain diffuse reflectance and/or fluorescence spectra measurements of the tumor, and an algorithm may be used to extract the optical properties (i.e., determine absorption, scattering, and/or intrinsic fluorescence data properties). These properties may be associated with quantities of biomarkers present in the tumor, and may be used to determine tumor characteristics including, but not limited to, tumor size or shape. For example, biomarkers present in tumor tissue may be quantitatively measured to determine the current oxygen depletion and blood vessel growth of the tumor.

In block 404, the biomarker measurements are analyzed. In one embodiment, the biomarker measurements may be used to make a prognostic assessment of the tumor. If the size of a tumor can be identified, the best course of therapy to treat the tumor may then be determined. One example is utilizing the data on the current oxygen depletion and blood vessel growth to identify a tumor and select a favorable treatment/therapy, e.g., chemotherapy (or regimen thereof) or radiotherapy.

In block 406, the chosen therapy is initiated. In one embodiment, various cancer fighting drugs may be prescribed in order to possibly reduce the size of the tumor (e.g., chemotherapy).

In block 408, the progress of the therapy may be monitored through the measurement of known biomarkers. Monitoring may occur through taking current measurements of the biomarkers which were initially measured. These measurements may allow for a comparison between the current biomarker concentrations and the initial biomarker concentrations. In one embodiment, an instrument (e.g., a cannula) may be used to position probe 102 (or probe 211) on the tumor in vivo in a similar manner described in block 402. Probe 102 (or probe 211) may subsequently obtain the fluorescence and diffuse reflectance (or diffuse reflectance only) spectra measurements of the tumor and the algorithm may extract the optical properties (i.e., obtain absorption, scattering, and/or intrinsic fluorescence data) from the spectra data. For example, this may include measuring the current biomarker concentrations of the tumor to determine the present oxygen depletion levels and blood vessel growth associated with the tumor.

In block 410, a determination may be made as to whether the chosen therapy has produced positive results. This determination may be made by comparing the current biomarker concentrations to the initial biomarker concentrations and analyzing the results with respect to the anticipated response. If positive results have been produced, then method 400 continues to block 412. If positive results have not been produced, then method 400 continues to block 414. In one embodiment, the concentrations of biological markers may be used to determine whether the tumor has decreased in size. For example, it may be determined that the tumor has decreased by identifying an indication of a decrease in blood vessel growth and oxygen depletion in comparison with the measurements obtained in block 402.

In block 412, the original therapy form may be continued. In one embodiment, the patient may continue to follow with his currently prescribed treatment if a decrease in tumor size has been detected. One example is to continue treating a patient with currently prescribed cancer fighting drugs.

Additionally, if therapy has been determined to produce successful results in block 410, method 400 may loop back to block 408 where the therapy form may be continued and monitored again. It may also be beneficial to continue to monitor the progress of therapy via biomarker concentration measurement, as described above, to determine if the positive response continues during the course of treatment. One embodiment may include monitoring the patient several times during treatment to assess the size of a tumor at different time intervals during treatment. Examples may include the monitoring and assessing the progress of treatment every two weeks as a patient undergoes therapy.

In block 414, the current therapy form may be discontinued. Possible examples of non-positive results include, but are not limited to, no change in condition or a worsening in condition. In one embodiment, the current therapy method may be abandoned in favor of another if no decrease in tumor size has been detected. One example is to abandon the currently prescribed cancer fighting drugs if biological markers indicate these drugs have no effect on the tumor.

In block 416, the biomarker measurements may be re-evaluated, and a new form of therapy may be chosen to treat the tumor. In one embodiment, the data on the biological markers may be re-evaluated in order to determine a different form of therapy that is likely to decrease the presence of these biomarkers. One example is to choose a different cancer drug combination which may result in a decrease of the tumor. Additionally, if the original therapeutic method has been deemed unsuccessful, therapy may begin again with the new chosen therapeutic method, per block 406. In one embodiment, a new form of therapy may be implemented and the progress of the therapy is monitored to determine if the new therapeutic method will be successful in decreasing the size of the tumor. One exemplary scenario may involve a beginning a new therapeutic method involving different cancer fighting drugs to decrease a tumor which had been unresponsive to the original drug combination.

Figure 5:
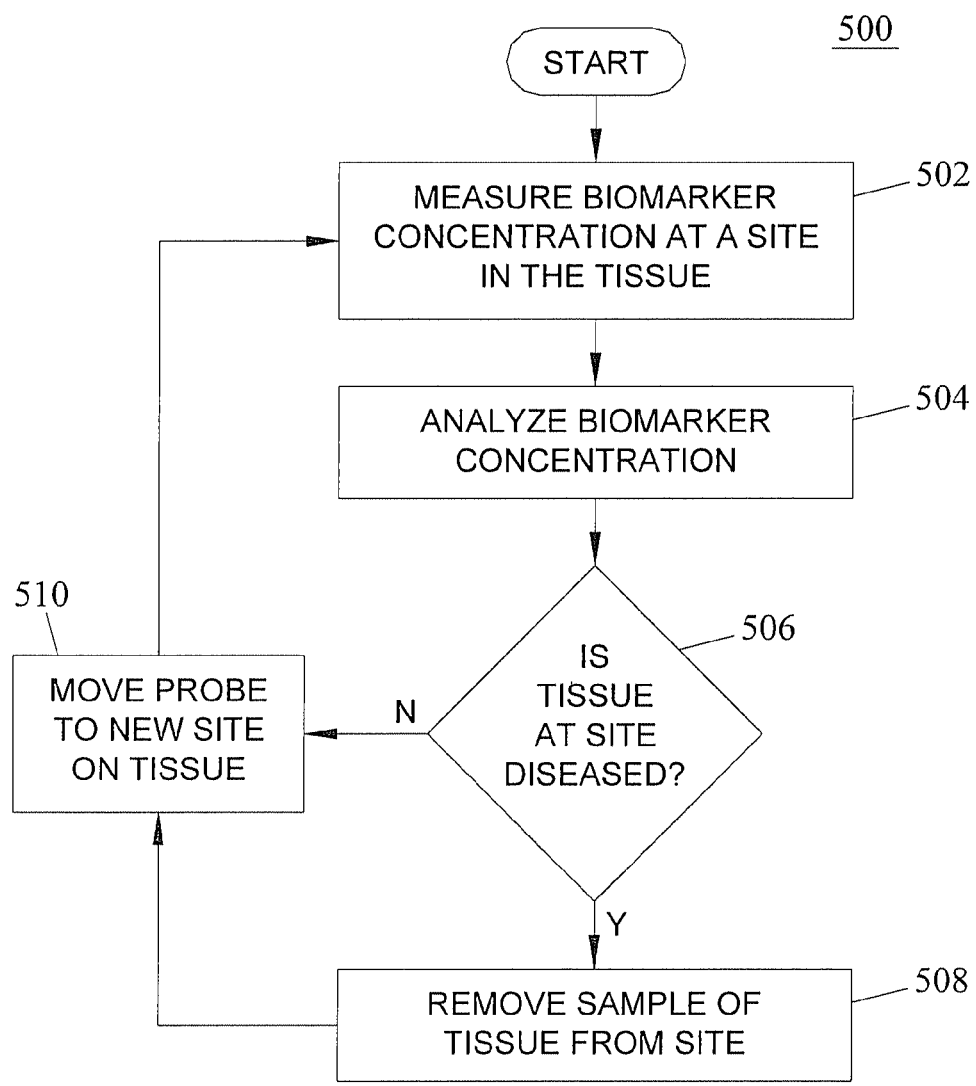
FIG. 5 is a flow chart of an exemplary process for measuring biomarker concentrations for diagnostic applications according to an embodiment of the subject matter described herein.

In addition to the therapeutic applications afforded, the present subject matter may also be utilized for diagnostic applications. FIG. 5 depicts one embodiment where the present subject matter may include a method 500 for diagnostic screening. Referring to FIG. 5, in block 502, biomarker measurements are taken at a tissue site of interest. In one embodiment, biomarker measurements are taken at a tissue site using an optical fiber probe. One example is to measure the biomarkers present at a tissue site which may appear suspicious on an ultrasound or X-ray image.

In block 504, the biomarker concentration may be analyzed. In one embodiment, the biomarker concentration may be analyzed by taking the measured data from probe 102 or 211, applying an algorithm to the data, and retrieving the optical properties. One example is to determine the concentration of a biomarker known to be associated with cancer by applying the measured data to a Monte Carlo or a diffusion algorithm and determining the optical properties (i.e., the absorption, scattering, and/or intrinsic fluorescence data) which can then yield concentrations.

In block 506, a determination may be made as to whether the tissue site is diseased. If the tissue is diseased, then method 500 continues to block 508. If the tissue is not diseased, then method 500 proceeds to block 510. Diseased sites may be characterized by several biomarker indicators including, but not limited to, abnormally high or low concentration levels in certain biomarkers. One embodiment may be determining whether the tissue at the site possesses biomarkers in concentrations which would indicate the tissue is not healthy. For example, the biomarker concentration data is used to determine if a suspicious tissue site originally viewed in an ultrasound or X-ray image is malignant, benign, or normal.

In block 508, a sample of the site of interest may be removed. One embodiment may be to remove a sample of tissue from a diseased site using removal methods known in the art. For example, a tissue sample is removed if the biomarkers indicate the site is cancerous. The sample may then be further tested to confirm the diagnosis or discern additional properties related to the disease.

In block 510, probe 102 (or 211) may be moved to a new site of interest. One embodiment may be to move probe 102 (or 211) to a different location on the tissue being investigated. If the site is determined to not be diseased or if a sample of the diseased site has already been removed, probe 102 (or 211) may be moved to a new site of interest. Method 500 may then be repeated several times to further survey the site. Such surveys may allow for the diagnosis of the extent of the disease present in the site, and may also allow for the identification of non-diseased areas which may then be spared from treatment. One example is to move probe 102 (or 211) to a different location on a suspicious tissue mass located via ultrasound or at the physcan's discretion.

Additional sites may be investigated by returning to block 502. One embodiment may be to make several measurements on and around a site of interest to determine the extent of a disease. One example is to measure biomarker concentrations that are indicative of cancer on and around a tumor to determine the size of the tumor.

The methods described by the present subject matter may be used for additional purposes and applications. In addition to therapeutic and diagnostic monitoring, the present subject matter may be used for applications such as monitoring tissue oxygenation in reconstructive/plastic/cosmetic surgery, drug discovery, cancer detection, monitoring response to therapy, measuring prognostic biomarkers, monitoring blood loss, providing biopsy guidance, evaluating trauma patients, transplant organ perfusion, and the like.

In an alternate embodiment, the aforementioned fiber optic probe may also be used for obtaining in vivo measurements of blood parameters. For example, the fiber optic probe may be used to quantitatively determine the concentration of "total hemoglobin" (i.e., the total hemoglobin content in a tissue mass), blood loss, dilutional effects from fluid intake, porphyrin levels, cellular metabolism, and the hemoglobin saturation of a tissue mass in vivo. In addition, the constituents of hemoglobin, which include oxyhemoglobin, deoxyhemoglobin, carboxyhemoglobin, and methemoglobin, may also be readily quantified using the present subject matter. The fiber optic probe may also measure the concentration of the hemoglobin analyte by being placed in an oral mucosa, under the tongue, or taped to any exposed surfaces (such as an arm), thereby providing real-time measurements of the analyte of interest. Applications of this technology include, but are not limited to, a quick non-invasive screening test for total hemoglobin, quantifying tissue blood loss in vivo, quantifying dilutional effects of fluids in the tissue, and quantifying tissue oxygenation in vivo. One other advantage of the present subject matter includes eliminating the need for all handling and disposal of blood and sharp medical equipment (e.g., syringes).

In one embodiment, the fiber optic probe may be used to perform intraoperative margin assessments of a tissue mass in vivo. Due to the fact that cancerous mass specimens removed from numerous patients can be characterized as having "positive margins." The existence of a positive margin in an excised tissue mass serves as an indication that cancerous tissue most likely remains in the patient. As a result, a repeat surgery is oftentimes required. In one embodiment, the present subject matter serves as an intraoperative instrument that ensures that a cancerous tissue mass is completely excised at the time of the surgery. One advantage of the present subject matter is that unlike existing techniques for evaluating tissue margins during surgery (e.g., cytology and frozen section), an on-site pathologist is not required.

The technology development for this application is an optical margin assessment device (e.g., a fiber optic probe), which permits surgeons to identify and correct "positive tumor margins" that exist during surgery. In order to enhance the effectiveness of identifying positive tumor margins utilizing optical spectroscopy, one or more contrast agents (e.g., acetic acid, Acriflavin, 2-[N-(7-nitrobenz-2-oxa-1,3-diazol-4-yl) amino]-2-deoxy-D-glucose (NBDG), fluorescin, and the like) may be used in conjunction with the fiber optic probe. For example, acetic acid may be used during colposcopic examination to identify atypical areas of the cervix that require biopsy. Application of acetic acid in a concentration ranging from 3-6% causes acetowhitening of cervical abnormalities, such as neoplasia, adenocarcinoma, and invasive squamous cell carcinoma. Specifically, the use of acetic acid may alter a tissue's protein structure such that light is prevented from passing through the epithelium, thereby enhancing light scattering. In another embodiment, the mere presence of the contrast agent in the tissue provides light scattering, fluorescence, or absorption contrast in the tissue mass. For example, 2-NBDG is a fluorescent optical analog of deoxyglucose (similar to 2-fluorodeoxyglucose used in Positron emission tomography (PET) imaging) and is taken up with increased glucose metabolism. In this scenario, the presence of the 2-NBDG in the tissue mass provides fluorescence contrast in the tissue mass. Likewise, Acriflavin intercalates with DNA and thus provides nuclear contrast. Acetic acid may be imaged via light scattering while Acriflavin and 2-NBDG fluoresce in the blue-green wavelengths. Notably, the present subject matter may use contrast agents to increase contrast between positive and negative margins in tissue, either in vivo or ex vivo.

In one embodiment, a contrast agent may be applied to internal tissue that is left exposed after the excision of a tumor tissue mass. For example, the tissue margins are "painted" with 3-6% acetic acid. The tissue margin surface is then imaged with a CCD camera, digital camera, or the like. The light source may be the surrounding ambient light or an illumination source that provides broadband illumination over the visible and near infrared wavelengths. The images may be captured rapidly over a period of 30-60 seconds during which the acetowhitening affect decays. The images derived from optical spectroscopy imaging techniques can capture and quantify the contrast agent's brightness and kinetics of the brightness to indicate whether the tumor margin is positive or negative (e.g., the contrast agent enhances light scattering in the margins of the tissue mass). More specifically, the contrast achieved may be enhanced by the use of a specific optical contrast agent that is selectively taken up by positive tumor margins. This information (i.e., the enhanced light scattering) is captured and processed using special signal processing algorithms to delineate positive tumor margins.

In an alternate embodiment, other contrast agents that are applicable to intraoperative margin assessment may be used. For example, photosensitizers such as aminolevulinic acid, methylene blue, and other porphyrins may be utilized. These contrast agents can also be used with a high dose of light to treat residual tumors in the cavity after resection.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A system for determining biomarker concentrations in a tissue mass, the system comprising:
    an instrument for inserting into the tissue mass;
    a fiber optic probe for interfacing the tissue mass upon being inserted into the instrument and measuring turbid spectral data of the tissue mass, wherein measuring the turbid spectral data includes conducting fluorescence spectral measurements and diffuse reflectance measurements of the tissue mass simultaneously, wherein the fiber optic probe is a forward firing fiber optic probe that includes a probe tip comprising a plurality of centrally grouped illumination fibers that are concentrically surrounded by a plurality of collection fiber rings, wherein each of the collection fiber rings consists of a plurality of ring-specific collection fibers or a plurality of ring-specific collection fibers and a plurality of dead fibers; and
    a processing unit for converting the turbid spectral data to absorption, scattering, and intrinsic fluorescence spectral data via a Monte Carlo algorithm or a diffusion algorithm and quantifying biomarker concentrations in the tissue mass using the absorption, scattering, and intrinsic fluorescence spectral data, wherein the intrinsic fluorescence spectral data is corrected to account for the absorption and scattering data.

2. The system of claim 1 wherein the fiber optic probe fits within a biopsy needle or a biopsy cannula.

3. The system of claim 2 wherein the biopsy needle includes at least one of a Suros 9G biopsy needle, a Mammotome biopsy needle, a Bard Vacora 10G biopsy needle, a Bard Vacora 14G biopsy needle, and a Cardinal Achieve 14G biopsy needle.

4. The system of claim 1 wherein the instrument comprises a cannula, a biopsy needle, an endoscopic instrument, and a laparoscopic instrument.

5. The system of claim 1 wherein the turbid spectral data comprises diffuse reflectance spectral data and fluorescence spectral data of the tissue mass.

6. The system of claim 1 wherein the biomarker concentrations are used to determine if the tissue mass is malignant, benign, or normal, or are used to quantify drug uptake by the tissue mass.

7. The system of claim 6 wherein a biopsy is conducted on the tissue mass through a cannula or a biopsy needle if the tissue is malignant.

8. The system of claim 1 wherein the fiber optic probe is adapted to acquire the turbid spectral data using a spectrometer having a spectral bandpass of between about 2.5 nm and 5 nm.

9. The system of claim 1 wherein the Monte Carlo algorithm includes either an inverse Monte Carlo reflectance algorithm or an inverse Monte Carlo fluorescence algorithm.

10. The system of claim 1 wherein the processing unit is further configured to determine the concentrations at least one of total hemoglobin, oxyhemoglobin concentration, deoxyhemoglobin concentration, beta carotene concentration, hemoglobin saturation, nicotinamide adenine dinucleotide (NADH), flavin adenine dinucleotide (FAD), collagen, porphyrins, retinol, tryptophan, tissue blood loss, dilutional effects of fluids, in vivo.

11. A method for determining biomarker concentrations in a tissue mass, the method comprising:
    inserting an instrument into the tissue mass;
    applying a fiber optic probe upon being inserted into the instrument into the tissue mass, wherein the fiber optic probe is a forward firing fiber optic probe that includes a probe tip comprising a plurality of centrally grouped illumination fibers that are concentrically surrounded by a plurality of collection fiber rings, wherein each of the collection fiber rings consists of a plurality of ring-specific collection fibers or a plurality of ring-specific collection fibers and a plurality of dead fibers;
    measuring turbid spectral data of the tissue mass using the fiber optic probe, wherein measuring the turbid spectral data includes conducting fluorescence spectral measurements and diffuse reflectance measurements of the tissue mass simultaneously;
    converting the turbid spectral data to absorption, scattering, and intrinsic fluorescence spectral data via a Monte Carlo algorithm or a diffusion algorithm; and
    quantifying biomarker concentrations in the tissue mass using the at least one of absorption, scattering, and intrinsic fluorescence spectral data, wherein the intrinsic fluorescence spectral data is corrected to account for the absorption and scattering data.

12. The method of claim 11 wherein the fiber optic probe is adapted to fit within a biopsy needle or a biopsy cannula.

13. The method of claim 12 wherein the biopsy needle includes at least one of a Suros 9G biopsy needle, a Mammotome biopsy needle, a Bard Vacora 10G biopsy needle, a Bard Vacora 14G biopsy needle, and a Cardinal Achieve 14G biopsy needle.

14. The method of claim 11 wherein the instrument comprises a cannula, a biopsy needle, an endoscopic instrument, and a laparoscopic instrument.

15. The method of claim 11 wherein the turbid spectral data comprises diffuse reflectance spectral data and fluorescence spectral data of the tissue mass.

16. The method of claim 11 wherein the biomarker concentrations are used to determine if the tissue mass is malignant, benign, or normal, or are used to quantify drug uptake by the tissue mass.

17. The method of claim 16 wherein a biopsy is conducted on the tissue mass through a cannula or a biopsy needle if the tissue is malignant.

18. The method of claim 11 wherein the fiber optic probe is adapted to acquire the turbid spectral data using a spectrometer having a spectral bandpass of between about 2.5 nm and 5 nm.

19. The method of claim 11 wherein the Monte Carlo algorithm includes either an inverse Monte Carlo reflectance algorithm or an inverse Monte Carlo fluorescence algorithm.

20. The method of claim 11 further comprising: applying a contrast agent to the tissue mass to enhance light scattering, absorption, or fluorescence in the tissue mass.

21. The method of claim 20 wherein the enhanced light scattering, absorption, or fluorescence aids with margin assessment.

22. The method of claim 20 wherein the contrast agent includes at least one of acetic acid, Acriflavin, 2-2-deoxy-D-glucose (NBDG), fluorescin, aminolevulinic acid, and methylene blue.

23. The method of claim 11 wherein the processing unit is further configured to determine the concentrations at least one of total hemoglobin, oxyhemoglobin concentration, deoxyhemoglobin concentration, beta carotene concentration, nicotinamide adenine dinucleotide (NADH), flavin adenine dinucleotide (FAD), collagen, retinol, porphyrin, hemoglobin saturation, tissue blood loss, dilutional effects of fluids in vivo.

* * * * *